United States Patent
Yu et al.

(10) Patent No.: US 8,962,236 B2
(45) Date of Patent: Feb. 24, 2015

(54) EPIGENETIC BIOMARKER ADAMTS9 FOR DIAGNOSIS AND PROGNOSIS OF GASTRIC CANCER

(71) Applicant: The Chinese University of Hong Kong, Shatin, New Territories (CN)

(72) Inventors: Jun Yu, Lake Silver (CN); Joseph Jao Yiu Sung, Man On san (CN)

(73) Assignee: The Chinese University of Hong Kong, Shatin, N.T. (HK)

( * ) Notice: Subject to any disclaimer, the term of this patent is extended or adjusted under 35 U.S.C. 154(b) by 0 days.

(21) Appl. No.: 13/797,300

(22) Filed: Mar. 12, 2013

(65) Prior Publication Data

US 2014/0274908 A1    Sep. 18, 2014

(51) Int. Cl.
  *C07K 14/435* (2006.01)
  *C12Q 1/68* (2006.01)
  *G01N 33/68* (2006.01)

(52) U.S. Cl.
  CPC ............ *C07K 14/435* (2013.01); *C12Q 1/6886* (2013.01); *G01N 33/6893* (2013.01)
  USPC .................................................. 435/4; 435/6

(58) Field of Classification Search
  CPC ............................ C07K 14/435; C12Q 1/6886
  See application file for complete search history.

(56) References Cited

FOREIGN PATENT DOCUMENTS

WO    WO2007143037    * 12/2007

OTHER PUBLICATIONS

Du et al, Oncogene 32:3319-28, published online Aug. 2012.*
Zhang et al, Can Genetics and Cytogeneties 196:38-44, 2010.*

* cited by examiner

*Primary Examiner* — Lei Yao
(74) *Attorney, Agent, or Firm* — Kilpatrick Townsend & Stockton LLP

(57) ABSTRACT

The present invention provides a method for diagnosing and determining prognosis of gastric cancer in a subject by detecting suppressed expression of the ADAMTS9 gene, which in some cases is due to elevated methylation level in the genomic sequence of this gene. A kit and device useful for such a method are also provided. In addition, the present invention provides a method for treating gastric cancer by increasing ADAMTS9 gene expression or activity.

7 Claims, 11 Drawing Sheets

EPIGENETIC BIOMARKER ADAMTS9 FOR DIAGNOSIS AND PROGNOSIS OF GASTRIC CANCER

REFERENCE TO A "SEQUENCE LISTING," A TABLE, OR A COMPUTER PROGRAM LISTING APPENDIX SUBMITTED AS AN ASCII TEXT FILE

The Sequence Listing written in file-134.TXT, created on May 6, 2013, 40,960 bytes, machine format IBM-PC, MS-Windows operating system, is hereby incorporated by reference in its entirety for all purposes.

BACKGROUND OF THE INVENTION

Gastric cancer, also known as stomach cancer, is the fourth most common cancer worldwide with approximately 1,000,000 cases diagnosed annually. It is a disease with a high mortality rate (about 800,000 deaths per year), making it the second most common cause of cancer death worldwide after lung cancer. The incidence of gastric cancer is significantly higher among men and in developing nations, including many Asian countries.

Gastric cancer often remains asymptomatic or exhibits only nonspecific symptoms in its early stages, diagnosis in many cases is therefore not made until the disease has reached an advanced stage. This leads to a generally poor prognosis: metastasis occurs in 80-90% of individuals diagnosed with gastric cancer, with a six-month survival rate of 65% in those diagnosed in early stages and less than 15% of those diagnosed in late stages.

Because of the prevalence of gastric cancer and its grave implications on patients' life expectancy, there exists a need for new methods to diagnose, monitor, and treat gastric cancer. This invention fulfills this and other related needs.

BRIEF SUMMARY OF THE INVENTION

In a first aspect, the present invention provides a method for detecting gastric cancer in a subject. The method includes the steps of: (a) measuring expression level of ADAMTS9 in a sample taken from the subject, and (b) comparing the expression level obtained in step (a) with a standard control. When a decrease in the expression level of ADAMTS9 is detected as compared with the standard control, it indicates that the subject may have gastric cancer. Typically, the sample used in the method is a stomach mucosa sample, e.g., one that includes stomach epithelial cells.

In some embodiments, the expression level of ADAMTS9 is the ADAMTS9 protein level. In other embodiments, the expression level of ADAMTS9 is ADAMTS9 mRNA level. When the ADAMTS9 protein level is measured, step (a) may include an immunoassay using an antibody that specifically binds the ADAMTS9 protein. For example, a Western Blot analysis may be used. In other cases, step (a) may involve mass spectrometry, or a hybridization-based assay such as hybridization to a microarray, fluorescence probe, or molecular beacon.

When ADAMTS9 mRNA level is measured, step (a) in some cases may involve an amplification reaction, such as a polymerase chain reaction (PCR), especially a reverse transcriptase-PCR (RT-PCR). In other cases, the detecting step may involve a polynucleotide hybridization assay, such as a Southern Blot analysis or Northern Blot analysis or an in situ hybridization assay. For example, a polynucleotide probe may be used in the polynucleotide hybridization assay to hybridize with SEQ ID NO:2, 3 or 4 or a complement thereof. In some cases, the polynucleotide probe may include a detectable moiety.

In some embodiments, when the subject is indicated as having gastric cancer after the first round of method steps described above, the claimed method may further include repeating step (a) at a later time using the same type of sample from the subject. An increase in the expression level of ADAMTS9 at the later time as compared to the amount from the original step (a) indicates an improvement of gastric cancer, whereas a decrease indicates a worsening of gastric cancer.

In a second aspect, the present invention provides another method for detecting gastric cancer in a subject. The method includes the steps of: (a) treating a sample taken from the subject with an agent that differentially modifies methylated and unmethylated DNA; and (b) determining whether each CpG in a CpG-containing genomic sequence is methylated or unmethylated, with the CpG-containing genomic sequence being at least a segment of SEQ ID NO:1, 6 or 7 and comprising at least one CpG. When the presence of one methylated CpG is detected in the CpG-containing genomic sequence, it indicates that the subject may have gastric cancer.

In some embodiments, the CpG-containing genomic sequence contains two or more CpG, and when at least 50% of all CpG being methylated the subject is indicated as having gastric cancer. In some cases, the CpG-containing genomic sequence is a segment of at least 15, 20, 50, or more contiguous nucleotides of SEQ ID NO: 1, 6 or 7. In other cases, the CpG-containing genomic sequence is SEQ ID NO: 1, 6 or 7. In one embodiment of the claimed method, the CpG-containing genomic sequence is SEQ ID NO: 1, and when at least 2 of all CpG in the CpG-containing genomic sequence are methylated, the subject is indicated as likely having gastric cancer. In one embodiment of the claimed method, the CpG-containing genomic sequence is SEQ ID NO: 1, and when at least 13 of all CpG in the CpG-containing genomic sequence are methylated, the subject is indicated as likely having gastric cancer.

In some examples, the sample used in the claimed method is a gastric tissue sample. In other examples, the sample used in the claimed method is a stomach mucosa sample. In some examples, the gastric tissue sample or stomach mucosa samples is a tumor sample.

In some examples, when the subject is indicated as having gastric cancer after the first round of method steps described above, the method further involves repeating steps (a) and (b) at a later time using the sample type of sample from the subject. When an increase is detected in the number of methylated CpG at the later time as compared to the number of methylated CpG determined from the original step (b), it indicates a worsening of gastric cancer, whereas a decrease indicates an improvement of gastric cancer.

In some embodiments, the agent used in the claimed method to differentially modify methylated DNA and unmethylated DNA is an enzyme that preferentially cleaves methylated DNA, an enzyme that preferentially cleaves unmethylated DNA, or a bisulfite. In other embodiments, step (b) of the method involves an amplification reaction; or step (b) may involve sequencing of a DNA molecule.

In some embodiments, the amplification reaction is a polymerase chain reaction (PCR). In some cases the PCR reaction comprises a pair of oligonucleotide primers having the nucleotide sequence set forth in SEQ ID NOs: 10 and 11. In some embodiments, the amplification reaction is followed by DNA sequencing. In some embodiments, the amplification reaction is a methylation-specific polymerase chain reaction (MSP).

In some cases the MSP reaction comprises a pair of oligonucleotide primers having the nucleotide sequence set forth in SEQ ID NOs: 12 and 13 and/or a pair of oligonucleotide primers having the nucleotide sequence set forth in SEQ ID NOs: 14 and 15.

In some embodiments, the method further comprises performing a diagnostic assay to the subject identified as having an increase in the expression level of ADAMTS9. Non-limiting examples of a diagnostic assay include an imaging test, such as, computerized tomography (CT), positron emission tomography (PET), magnetic resonance imaging (MRI), or exploratory surgery, such as, laparoscopy. In some embodiments, the method further comprises administering a therapy directed to ameliorating gastric cancer to the subject identified as having an increase in the expression level of ADAMTS9. Non-limiting examples of a therapy for ameliorating gastric cancer include surgery, e.g., endoscopic mucosal resection, subtotal gastrectomy, and total gastrectomy, radiation therapy, chemotherapy, administration of targeted therapy drugs, e.g., trastuzumab (Herceptin), or a combination thereof. As described herein, an increase in the expression level of ADAMTS9 includes an increase in ADAMTS9 RNA level of ADAMTS9 protein level compared to a standard control, or the presence of at least one methylated CpG in the CpG-containing genomic sequence.

In a third aspect, the present invention provides a kit for detecting gastric cancer in a subject, comprising (1) a standard control that provides an average amount of ADAMTS9 protein or ADAMTS9 mRNA; and (2) an agent that specifically and quantitatively identifies ADAMTS9 protein or ADAMTS9 mRNA in a particular type of sample, e.g., a gastric tissue sample. In some cases, the agent may be an antibody that specifically binds the ADAMTS9 protein (SEQ ID NO: 5) or a portion thereof; or the agent may be a polynucleotide probe that hybridizes with the ADAMTS9 mRNA (SEQ ID NO:3). For example, the polynucleotide probe has the nucleotide sequence set forth in SEQ ID NO:2, 3 or 4 or a complement thereof. The agent may include a detectable moiety. In other cases, the kit may further comprise two oligonucleotide primers for specifically amplifying at least a segment of SEQ ID NO:2, 3 or 4 or its complement in an amplification reaction. In some instances, the two oligonucleotide primers comprise the nucleotide sequence set forth in SEQ ID NOs:8 and 9. Typically, the kit will further include an instruction manual.

In a fourth aspect, the present invention provides a method for inhibiting growth of a gastric cancer cell. The claimed method includes the step of contacting the gastric cancer cell with (1) an effective amount of a polypeptide that comprises the amino acid sequence set forth in SEQ ID NO:5 or (2) a nucleic acid that comprises a polynucleotide sequence encoding SEQ ID NO:5. In some embodiments, the nucleic acid is an expression cassette comprising a promoter operably linked to the polynucleotide sequence encoding SEQ ID NO:5. Various promoters may be useful in this method, for example, the promoter may be an epithelium-specific promoter. In other embodiments, the nucleic acid comprises the polynucleotide sequence set forth in SEQ ID NO:2. In yet other embodiments, the gastric cancer cell is within a patient's body.

In a fifth aspect, the present invention provides an isolated nucleic acid having the nucleotide sequence at least 95% identical to a segment of about 20-100 contiguous nucleotides of SEQ ID NO: 1-4, 6-14 or 15 or complement thereof. In some embodiments, the nucleic acid has the nucleotide sequence identical to a segment of about 20-100 contiguous nucleotides of SEQ ID NO: 1-4, 6-14 or 15 or complement thereof. In other embodiments, the nucleic acid is conjugated to a detectable moiety.

In addition, the present invention provides a kit for detecting gastric cancer. The kit comprises: (1) an agent that differentially modifies methylated and unmethylated DNA, and (2) an indicator that, after the agent has been used to treat a sample from a subject who is being tested for gastric cancer, determines whether each CpG in a CpG-containing genomic sequence is methylated or unmethylated. The CpG-containing genomic sequence is at least a segment of SEQ ID NO:1, 6 or 7 and comprises at least one CpG. The present invention also provides a composition for inhibiting growth of a gastric cancer cell. The composition contains an effective amount of (1) a polypeptide comprising the amino acid sequence set forth in SEQ ID NO:5 (e.g., a polypeptide consisting of the amino acid sequence of SEQ ID NO:5) or (2) a nucleic acid comprising or consisting of a polynucleotide sequence encoding SEQ ID NO:5 (e.g., a nucleic acid sequence comprising the polynucleotide sequence of SEQ ID NO:2 or 3), and a pharmaceutically acceptable carrier. In this regard, this invention further provides the use of a polypeptide comprising the amino acid sequence set forth in SEQ ID NO:5 (e.g., a polypeptide consisting of the amino acid sequence of SEQ ID NO:5) or a nucleic acid comprising a polynucleotide sequence encoding SEQ ID NO:2 or 3 (e.g., a nucleic acid sequence comprising or consisting of the polynucleotide sequence of SEQ ID NO:2 or 3) in preparing a medicament for inhibiting growth of a gastric cancer cell. Moreover, the present invention provides a use of a polynucleotide sequence that comprises or consists of a segment of SEQ ID NO:1, 2, 3, 4, 6 or 7 or complement thereof in preparing a kit for detecting gastric cancer. The segment is typically about 20-100 contiguous nucleotides of SEQ ID NO:1, 2, 3, 4, 6 or 7, or its complement.

DETAILED DESCRIPTION OF THE INVENTION

Figure 1:
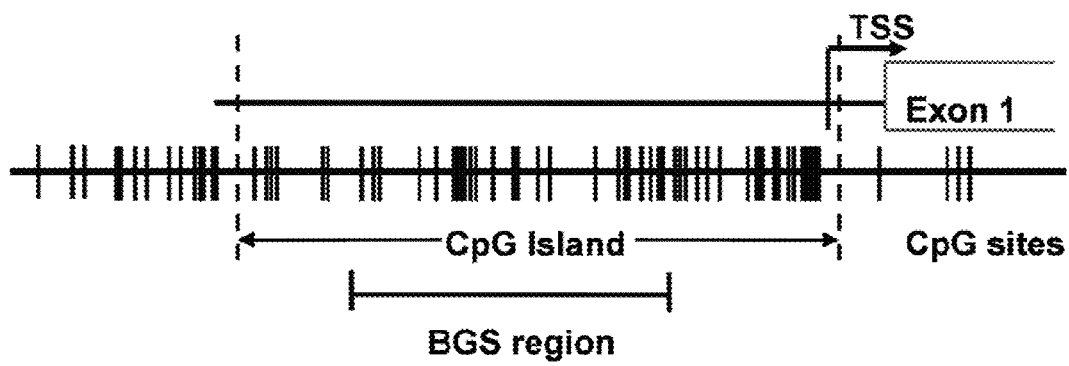
FIG. 1 shows ADAMTS9 CpG islands. ADAMTS9 is inactivated by promoter methylation in gastric cancer. The transcriptional start site and bisulfite genomic sequencing (BGS) region are indicated.

The term "ADAMTS9 gene" or "ADAMTS9 protein," as used herein, refers to any naturally occurring variants or mutants, interspecies homologs or orthologs, or man-made variants of human ADAMTS9 gene or ADAMTS9 protein. The human ADAMTS9 gene is located on chromosome 3p14.3. The cDNA sequence of a human wild-type ADAMTS9 gene is set forth in GenBank Accession No. NM_182920.2 (provided herein as SEQ ID NO:3), encoding a 1935-amino acid ADAMTS9 protein (provided herein as SEQ ID NO:5). An ADAMTS9 protein within the meaning of this application typically has at least 80%, or 90%, or 95% or higher sequence identity to the human wild-type ADAMTS9 protein.

In this disclosure the terms "gastric cancer" and "stomach cancer" have the same meaning and refer to a cancer of the stomach or of stomach cells. Such cancers may be adenocarcinomas that occur in the lining of the stomach (mucosa or stomach epithelium) and may be in pylorus, body, or cardial (lower, body and upper) parts of the stomach. A "gastric cancer cell" is a stomach epithelial cell possessing characteristics of gastric cancer and encompasses a precancerous cell, which is in the early stages of conversion to a cancer cell or which is predisposed for conversion to a cancer cell. Such cells may exhibit one or more phenotypic traits characteristic of the cancerous cells.

In this disclosure the term "or" is generally employed in its sense including "and/or" unless the content clearly dictates otherwise.

As used herein, the term "gene expression" is used to refer to the transcription of a DNA to form an RNA molecule encoding a particular protein (e.g., human ADAMTS9 protein) or the translation of a protein encoded by a polynucleotide sequence. In other words, both mRNA level and protein level encoded by a gene of interest (e.g., human ADAMTS9 gene) are encompassed by the term "gene expression level" in this disclosure.

In this disclosure the term "biological sample" or "sample" includes sections of tissues such as biopsy and autopsy samples, and frozen sections taken for histologic purposes, or processed forms of any of such samples. Biological samples include blood and blood fractions or products (e.g., serum, plasma, platelets, red blood cells, and the like), sputum or saliva, lymph and tongue tissue, cultured cells, e.g., primary cultures, explants, and transformed cells, stool, urine, stomach biopsy tissue etc. A biological sample is typically obtained from a eukaryotic organism, which may be a mammal, may be a primate and may be a human subject.

In this disclosure the term "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., tongue, colon, prostate, kidney, bladder, lymph node, liver, bone marrow, blood cell, stomach tissue, etc.) among other factors. Representative biopsy techniques include, but are not limited to, excisional biopsy, incisional biopsy, needle biopsy, surgical biopsy, and bone marrow biopsy and may comprise colonoscopy. A wide range of biopsy techniques are well known to those skilled in the art who will choose between them and implement them with minimal experimentation.

In this disclosure the term "isolated" nucleic acid molecule means a nucleic acid molecule that is separated from other nucleic acid molecules that are usually associated with the isolated nucleic acid molecule. Thus, an "isolated" nucleic acid molecule includes, without limitation, a nucleic acid molecule that is free of nucleotide sequences that naturally flank one or both ends of the nucleic acid in the genome of the organism from which the isolated nucleic acid is derived (e.g., a cDNA or genomic DNA fragment produced by PCR or restriction endonuclease digestion). Such an isolated nucleic acid molecule is generally introduced into a vector (e.g., a cloning vector or an expression vector) for convenience of manipulation or to generate a fusion nucleic acid molecule. In addition, an isolated nucleic acid molecule can include an engineered nucleic acid molecule such as a recombinant or a synthetic nucleic acid molecule. A nucleic acid molecule existing among hundreds to millions of other nucleic acid molecules within, for example, a nucleic acid library (e.g., a cDNA or genomic library) or a gel (e.g., agarose, or polyacrylamine) containing restriction-digested genomic DNA, is not an "isolated" nucleic acid.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain; it includes regions preceding and following the coding region (leader and trailer) involved in the transcription/translation of the gene product and the regulation of the transcription/translation, as well as intervening sequences (introns) between individual coding segments (exons).

In this application, the terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. For the purposes of this application, amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. For the purposes of this application, amino acid mimetics refers to chemical compounds that have a structure that is different from the general chemical structure of an amino acid, but that functions in a manner similar to a naturally occurring amino acid.

Amino acids may include those having non-naturally occurring D-chirality, as disclosed in WO01/12654, which may improve the stability (e.g., half life), bioavailability, and other characteristics of a polypeptide comprising one or more of such D-amino acids. In some cases, one or more, and potentially all of the amino acids of a therapeutic polypeptide have D-chirality.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

As used in herein, the terms "identical" or percent "identity," in the context of describing two or more polynucleotide or amino acid sequences, refer to two or more sequences or subsequences that are the same or have a specified percentage of amino acid residues or nucleotides that are the same (for example, a variant ADAMTS9 protein used in the method of this invention (e.g., for treating gastric cancer) has at least 80% sequence identity, preferably 85%, 90%, 91%, 92%, 93, 94%, 95%, 96%, 97%, 98%, 99%, or 100% identity, to a reference sequence, e.g., a wild-type human ADAMTS9 protein), when compared and aligned for maximum correspondence over a comparison window, or designated region as measured using one of the following sequence comparison algorithms or by manual alignment and visual inspection. Such sequences are then said to be "substantially identical." With regard to polynucleotide sequences, this definition also refers to the complement of a test sequence. Preferably, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Examples of algorithms that are suitable for determining percent sequence identity and sequence similarity are the BLAST and BLAST 2.0 algorithms, which are described in Altschul et al., (1990) *J. Mol. Biol.* 215: 403-410 and Altschul et al. (1977) *Nucleic Acids Res.* 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff and Henikoff, *Proc. Natl. Acad. Sci. USA* 89:10915 (1989)).

The BLAST algorithm also performs a statistical analysis of the similarity between two sequences (see, e.g., Karlin and Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

In this disclosure the terms "stringent hybridization conditions" and "high stringency" refer to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993) and will be readily understood by those skilled in the art. Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., Current Protocols in Molecular Biology, ed. Ausubel, et al.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter. "Operably linked" in this context means two or more genetic elements, such as a polynucleotide coding sequence and a promoter, placed in relative positions that permit the proper biological functioning of the elements, such as the promoter directing transcription of the coding sequence. Other elements that may be present in an expression cassette include those that enhance transcription (e.g., enhancers) and terminate transcription (e.g., terminators), as well as those that confer certain binding affinity or antigenicity to the recombinant protein produced from the expression cassette.

The term "bisulfite" as used herein encompasses all types of bisulfites, such as sodium bisulfite, that are capable of chemically converting a cytosine (C) to a uracil (U) without chemically modifying a methylated cytosine and therefore can be used to differentially modify a DNA sequence based on the methylation status of the DNA.

As used herein, a reagent that "differentially modifies" methylated or non-methylated DNA encompasses any reagent that reacts differentially with methylated and unmethylated DNA in a process through which distinguishable products or quantitatively distinguishable results (e.g. degree of binding or precipitation) are generated from methylated and non-methylated DNA, thereby allowing the identification of the DNA methylation status. Such processes may include, but are not limited to, chemical reactions (such as an unmethylated C→U conversion by bisulfite), enzymatic treatment (such as cleavage by a methylation-dependent endonuclease), binding, and precipitation. Thus, an enzyme that preferentially cleaves methylated DNA is one capable of cleaving a DNA molecule at a much higher efficiency when the DNA is methylated, whereas an enzyme that preferentially cleaves unmethylated DNA exhibits a significantly higher efficiency when the DNA is not methylated. In the context of the present invention, a reagent that "differentially modifies" methylated and unmethylated DNA also refers to any reagent that exhibits differential ability in its binding to DNA sequences or precipitation of DNA sequences depending on their methylation status. One class of such reagents consists of methylated DNA binding proteins.

A "CpG-containing genomic sequence" as used herein refers to a segment of DNA sequence at a defined location in the genome of an individual. Typically, a "CpG-containing genomic sequence" is at least 15 contiguous nucleotides in length and contains at least one CpG pair. In some cases, it can be at least 18, 20, 25, 30, 50, 80, 100, 150, 200, 250, or 300 contiguous nucleotides in length and contains at least 2, 3, 4, 5, 6, 7, 8, 9, 10, 15, 20, 25, or 30 CpG pairs. In some instances, a CpG-containing genomic sequence is a segment (e.g., portion) of a gene that contains the promoter and exon 1 of the gene, wherein the segment can be at least 15, 18, 20, 25, 30, 50, 80, 100, 150, 200, 250, or 300 contiguous nucleotides in length. For example, a CpG-containing genomic sequence can be 300 to 3,000 base pairs in length. For any one "CpG-containing genomic sequence" at a given location, e.g., within a region of the human ADAMTS9 genomic sequence (such as the region containing the promoter and exon 1), nucleotide sequence variations may exist from individual to individual and from allele to allele even for the same individual. Furthermore, a "CpG-containing genomic sequence" may encompass a nucleotide sequence transcribed or not transcribed for protein production, and the nucleotide sequence can be a protein-coding sequence, a non protein-coding sequence (such as a transcription promoter), or a combination thereof.

The term "immunoglobulin" or "antibody" (used interchangeably herein) refers to an antigen-binding protein having a basic four-polypeptide chain structure consisting of two heavy and two light chains, said chains being stabilized, for example, by interchain disulfide bonds, which has the ability to specifically bind antigen. Both heavy and light chains are folded into domains.

The term "antibody" also refers to antigen- and epitope-binding fragments of antibodies, e.g., Fab fragments, that can be used in immunological affinity assays. There are a number of well characterized antibody fragments. Thus, for example, pepsin digests an antibody C-terminal to the disulfide linkages in the hinge region to produce F(ab)'$_2$, a dimer of Fab which itself is a light chain joined to $V_H$-$C_H$1 by a disulfide bond. The F(ab)'$_2$ can be reduced under mild conditions to break the disulfide linkage in the hinge region thereby converting the (Fab')$_2$ dimer into an Fab' monomer. The Fab' monomer is essentially a Fab with part of the hinge region (see, e.g., Fundamental Immunology, Paul, ed., Raven Press, N.Y. (1993), for a more detailed description of other antibody fragments). While various antibody fragments are defined in terms of the digestion of an intact antibody, one of skill will appreciate that fragments can be synthesized de novo either chemically or by utilizing recombinant DNA methodology. Thus, the term antibody also includes antibody fragments either produced by the modification of whole antibodies or synthesized using recombinant DNA methodologies.

The phrase "specifically binds," when used in the context of describing a binding relationship of a particular molecule to a protein or peptide, refers to a binding reaction that is determinative of the presence of the protein in a heterogeneous population of proteins and other biologics. Thus, under designated binding assay conditions, the specified binding agent (e.g., an antibody) binds to a particular protein at least two times the background and does not substantially bind in a significant amount to other proteins present in the sample. Specific binding of an antibody under such conditions may require an antibody that is selected for its specificity for a particular protein or a protein but not its similar "sister" proteins. A variety of immunoassay formats may be used to select antibodies specifically immunoreactive with a particular protein or in a particular form. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity). Typically a specific or selective binding reaction will be at least twice background signal or noise and more typically more than 10 to 100 times background. On the other hand, the term "specifically bind" when used in the context of referring to a polynucleotide sequence forming a double-stranded complex with another polynucleotide sequence describes "polynucleotide hybridization" based on the Watson-Crick base-pairing, as provided in the definition for the term "polynucleotide hybridization method."

As used in this application, an "increase" or a "decrease" refers to a detectable positive or negative change in quantity from a comparison control, e.g., an established standard control (such as an average expression level of ADAMTS9 mRNA or protein found in non-cancerous stomach tissue). An increase is a positive change that is typically at least 10%, or at least 20%, or 50%, or 100%, and can be as high as at least 2-fold or at least 5-fold or even 10-fold of the control value. Similarly, a decrease is a negative change that is typically at least 10%, or at least 20%, 30%, or 50%, or even as high as at least 80% or 90% of the control value. Other terms indicating quantitative changes or differences from a comparative basis, such as "more," "less," "higher," and "lower," are used in this application in the same fashion as described above. In contrast, the term "substantially the same" or "substantially lack of change" indicates little to no change in quantity from the standard control value, typically within ±10% of the standard control, or within ±5%, 2%, or even less variation from the standard control.

A "polynucleotide hybridization method" as used herein refers to a method for detecting the presence and/or quantity of a pre-determined polynucleotide sequence based on its ability to form Watson-Crick base-pairing, under appropriate hybridization conditions, with a polynucleotide probe of a known sequence. Examples of such hybridization methods include Southern blot, Northern blot, microarray and in situ hybridization. A polynucleotide probe can be conjugated with a chemical moiety that generates a detectable fluorescent signal, such as but not limited to, a fluorescent moiety or a fluorochrome. In some cases, the probe is a molecular beacon.

"Primers" as used herein refer to oligonucleotides that can be used in an amplification method, such as a polymerase chain reaction (PCR), to amplify a nucleotide sequence based on the polynucleotide sequence corresponding to a gene of interest, e.g., the cDNA or genomic sequence for human ADAMTS9 or a portion thereof. Typically at least one of the PCR primers for amplification of a polynucleotide sequence is sequence-specific for that polynucleotide sequence. The exact length of the primer will depend upon many factors, including temperature, source of the primer, and the method used. For example, for diagnostic and prognostic applications, depending on the complexity of the target sequence, the oligonucleotide primer typically contains at least 10, or 15, or 20, or 25 or more nucleotides, although it may contain fewer nucleotides or more nucleotides. The factors involved in determining the appropriate length of primer are readily known to one of ordinary skill in the art. The primers used in particular embodiments are shown in Table 1 of the disclosure where their specific applications are indicated. In this disclosure the term "primer pair" means a pair of primers that hybridize to opposite strands a target DNA molecule or to regions of the target DNA which flank a nucleotide sequence to be amplified. In this disclosure the term "primer site", means the area of the target DNA or other nucleic acid to which a primer hybridizes.

A "label," "detectable label," or "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins that can be made detectable, e.g., by incorporating a radioactive component into the peptide or used to detect antibodies specifically reactive with the peptide. Typically a detectable label is attached to a probe or a molecule with defined binding characteristics (e.g., a polypeptide with a known binding specificity or a polynucleotide), so as to allow the presence of the probe (and therefore its binding target) to be readily detectable.

"Standard control" as used herein refers to a predetermined amount or concentration of a polynucleotide sequence or polypeptide, e.g., ADAMTS9 mRNA or protein, that is present in an established normal disease-free tissue sample, e.g., a normal stomach epithelial tissue sample. The standard control value is suitable for the use of a method of the present invention, to serve as a basis for comparing the amount of ADAMTS9 mRNA or protein that is present in a test sample. An established sample serving as a standard control provides an average amount of ADAMTS9 mRNA or protein that is typical for a stomach epithelial tissue sample (e.g., stomach mucosa) of an average, healthy human without any stomach disease especially gastric cancer as conventionally defined. A standard control value may vary depending on the nature of the sample as well as other factors such as the gender, age, ethnicity of the subjects based on whom such a control value is established.

The term "average," as used in the context of describing a human who is healthy, free of any stomach disease (especially gastric cancer) as conventionally defined, refers to certain characteristics, especially the amount of human ADAMTS9 mRNA or ADAMTS9 protein, found in the person's stomach tissue, e.g., epithelial tissue or gastric mucosa, that are representative of a randomly selected group of healthy humans who are free of any stomach diseases (especially gastric cancer). This selected group should comprise a sufficient number of humans such that the average amount of ADAMTS9 mRNA or protein in the stomach mucosa among these individuals reflects, with reasonable accuracy, the corresponding amount of ADAMTS9 mRNA/protein in the general population of healthy humans. In addition, the selected group of humans generally have a similar age to that of a subject whose stomach tissue sample is tested for indication of gastric cancer. Moreover, other factors such as gender, ethnicity, medical history are also considered and preferably closely matching between the profiles of the test subject and the selected group of individuals establishing the "average" value.

The term "amount" as used in this application refers to the quantity of a polynucleotide of interest or a polypeptide of interest, e.g., human ADAMTS9 mRNA or protein, present in a sample. Such quantity may be expressed in the absolute terms, i.e., the total quantity of the polynucleotide or polypeptide in the sample, or in the relative terms, i.e., the concentration of the polynucleotide or polypeptide in the sample.

The term "treat" or "treating," as used in this application, describes to an act that leads to the elimination, reduction, alleviation, reversal, or prevention or delay of onset or recurrence of any symptom of a relevant condition. In other words, "treating" a condition encompasses both therapeutic and prophylactic intervention against the condition.

The term "effective amount" as used herein refers to an amount of a given substance that is sufficient in quantity to produce a desired effect. For example, an effective amount of an polynucleotide encoding ADAMTS9 mRNA is the amount of said polynucleotide to achieve an increased level of ADAMTS9 protein expression or biological activity, such that the symptoms of gastric cancer are reduced, reversed, eliminated, prevented, or delayed of the onset in a patient who has been given the polynucleotide for therapeutic purposes. An amount adequate to accomplish this is defined as the "therapeutically effective dose." The dosing range varies with the nature of the therapeutic agent being administered and other factors such as the route of administration and the severity of a patient's condition.

The term "subject" or "subject in need of treatment," as used herein, includes individuals who seek medical attention due to risk of, or actual suffering from, gastric cancer. Subjects also include individuals currently undergoing therapy that seek manipulation of the therapeutic regimen. Subjects or individuals in need of treatment include those that demonstrate symptoms of gastric cancer or are at risk of suffering from gastric cancer or its symptoms. For example, a subject in need of treatment includes individuals with a genetic predisposition or family history for gastric cancer, those that have suffered relevant symptoms in the past, those that have been exposed to a triggering substance or event, as well as those suffering from chronic or acute symptoms of the condition. A "subject in need of treatment" may be at any age of life.

"Inhibitors," "activators," and "modulators" of ADAMTS9 protein are used to refer to inhibitory, activating, or modulating molecules, respectively, identified using in vitro and in vivo assays for ADAMTS9 protein binding or signaling, e.g., ligands, agonists, antagonists, and their homologs and mimetics. The term "modulator" includes inhibitors and activators. Inhibitors are agents that, e.g., partially or totally block carbohydrate binding, decrease, prevent, delay activation, inactivate, desensitize, or down regulate the activity of ADAMTS9 protein. In some cases, the inhibitor directly or indirectly binds to ADAMTS9 protein, such as a neutralizing antibody Inhibitors, as used herein, are synonymous with inactivators and antagonists. Activators are agents that, e.g., stimulate, increase, facilitate, enhance activation, sensitize or up regulate the activity of ADAMTS9 protein. Modulators include ADAMTS9 protein ligands or binding partners, including modifications of naturally-occurring ligands and synthetically-designed ligands, antibodies and antibody fragments, antagonists, agonists, small molecules including carbohydrate-containing molecules, siRNAs, RNA aptamers, and the like.

I. Introduction

Gastric cancer patients often face a grim prognosis due to the nature of this disease in its lacking of specific symptoms during its early development stages. Early detection of gastric cancer is therefore critical for improving patient survival rate.

The present inventors discovered for the first time that expression of ADAMTS9 protein is suppressed in gastric cancer cells. This suppressed expression of ADAMTS9 protein is due to increased methylation in the ADAMTS9 genomic sequence, especially in the promoter region of the gene, which leads to decreased transcription of ADAMTS9 mRNA. This discovery provides important means for detecting, monitoring, and treating gastric cancer.

II. General Methodology

Practicing this invention utilizes routine techniques in the field of molecular biology. Basic texts disclosing the general methods of use in this invention include Sambrook and Russell, *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage and Caruthers, *Tetrahedron Lett.* 22:1859-1862 (1981), using an automated synthesizer, as described in Van Devanter et. al., *Nucleic Acids Res.* 12:6159-6168 (1984). Purification of oligonucleotides is performed using any art-recognized strategy, e.g., native acrylamide gel electrophoresis or anion-exchange high performance liquid chromatography (HPLC) as described in Pearson and Reanier, *J. Chrom.* 255: 137-149 (1983).

The sequence of interest used in this invention, e.g., the polynucleotide sequence of the human ADAMTS9 gene, and synthetic oligonucleotides (e.g., primers) can be verified using, e.g., the chain termination method for sequencing double-stranded templates of Wallace et al., *Gene* 16: 21-26 (1981).

A. Acquisition and Preparation of Stomach Tissue Samples

A stomach tissue sample is obtained from a person to be tested or monitored for gastric cancer using a method of the present invention. The stomach tissue sample can be a cancer (tumor) sample or a non-cancer sample. Collection of stomach epithelial tissue (e.g., stomach mucosal tissue) sample from an individual is performed in accordance with the standard protocol hospitals or clinics generally follow, such as during an endoscopy. An appropriate amount of stomach epithelium is collected and may be stored according to standard procedures prior to further preparation.

The analysis of ADAMTS9 mRNA or DNA found in a patient's stomach epithelial sample according to the present invention may be performed using, e.g., stomach mucosa. The methods for preparing tissue samples for nucleic acid extraction are well known among those of skill in the art. For example, a subject's stomach mucosa sample should be first treated to disrupt cellular membrane so as to release nucleic acids contained within the cells.

B. Extraction and Quantitation of RNA

There are numerous methods for extracting mRNA from a biological sample. The general methods of mRNA preparation (e.g., described by Sambrook and Russell, *Molecular Cloning: A Laboratory Manual* 3d ed., 2001) can be followed; various commercially available reagents or kits, such as Trizol reagent (Invitrogen, Carlsbad, Calif.), Oligotex Direct mRNA Kits (Qiagen, Valencia, Calif.), RNeasy Mini Kits (Qiagen, Hilden, Germany), and PolyATtract® Series 9600™ (Promega, Madison, Wis.), may also be used to obtain mRNA from a biological sample from a test subject. Combinations of more than one of these methods may also be used.

It is essential that all contaminating DNA be eliminated from the RNA preparations. Thus, careful handling of the samples, thorough treatment with DNase, and proper negative controls in the amplification and quantification steps should be used.

1. PCR-Based Quantitative Determination of mRNA Level

Once mRNA is extracted from a sample, the amount of human ADAMTS9 may be quantified. The preferred method for determining the mRNA level is an amplification-based method, e.g., by polymerase chain reaction (PCR), especially reverse transcription-polymerase chain reaction (RT-PCR).

Prior to the amplification step, a DNA copy (cDNA) of the human ADAMTS9 (such as, for example, SEQ ID NO: 2 or a portion thereof) must be synthesized. This is achieved by reverse transcription, which can be carried out as a separate step, or in a homogeneous reverse transcription-polymerase chain reaction (RT-PCR), a modification of the polymerase chain reaction for amplifying RNA. Methods suitable for PCR amplification of ribonucleic acids are described by Romero and Rotbart in *Diagnostic Molecular Biology Principles and Applications* pp. 401-406; Persing et al., eds., Mayo Foundation, Rochester, Minn., 1993; Egger et al., *J. Clin. Microbiol.* 33:1442-1447, 1995; and U.S. Pat. No. 5,075,212.

The general methods of PCR are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available.

Although PCR amplification of the target mRNA is typically used in practicing the present invention. One of skill in the art will recognize, however, that amplification of these mRNA species in a maternal blood sample may be accomplished by any known method, such as ligase chain reaction (LCR), transcription-mediated amplification, and self-sustained sequence replication or nucleic acid sequence-based amplification (NASBA), each of which provides sufficient amplification. More recently developed branched-DNA technology may also be used to quantitatively determining the amount of mRNA markers in maternal blood. For a review of branched-DNA signal amplification for direct quantitation of nucleic acid sequences in clinical samples, see Nolte, *Adv. Clin. Chem.* 33:201-235, 1998.

2. Other Quantitative Methods

The ADAMTS9 mRNA can also be detected using other standard techniques, well known to those of skill in the art. Although the detection step is typically preceded by an amplification step, amplification is not required in the methods of the invention. For instance, the mRNA may be identified by size fractionation (e.g., gel electrophoresis), whether or not proceeded by an amplification step. After running a sample in an agarose or polyacrylamide gel and labeling with ethidium bromide according to well known techniques (see, e.g., Sambrook and Russell, supra), the presence of a band of the same size as the standard comparison is an indication of the presence of a target mRNA, the amount of which may then be compared to the control based on the intensity of the band. Alternatively, oligonucleotide probes specific to ADAMTS9 mRNA can be used to detect the presence of such mRNA species and indicate the amount of mRNA in comparison to the standard comparison, based on the intensity of signal imparted by the probe.

Sequence-specific probe hybridization is a well-known method of detecting a particular nucleic acid comprising other species of nucleic acids. Under sufficiently stringent hybridization conditions, the probes hybridize specifically only to substantially complementary sequences. The stringency of the hybridization conditions can be relaxed to tolerate varying amounts of sequence mismatch.

A number of hybridization formats well known in the art, including but not limited to, solution phase, solid phase, or mixed phase hybridization assays. The following articles provide an overview of the various hybridization assay formats: Singer et al., *Biotechniques* 4:230, 1986; Haase et al., *Methods in Virology*, pp. 189-226, 1984; Wilkinson, *In situ Hybridization*, Wilkinson ed., IRL Press, Oxford University Press, Oxford; and Hames and Higgins eds., *Nucleic Acid Hybridization: A Practical Approach*, IRL Press, 1987.

The hybridization complexes are detected according to well-known techniques. Nucleic acid probes capable of specifically hybridizing to a target nucleic acid, i.e., the mRNA or the amplified DNA, can be labeled by any one of several methods typically used to detect the presence of hybridized nucleic acids. One common method of detection is the use of autoradiography using probes labeled with $^3$H, $^{125}$I, $^{35}$S, $^{14}$C, or $^{32}$P, or the like. The choice of radioactive isotope depends on research preferences due to ease of synthesis, stability, and half-lives of the selected isotopes. Other labels include compounds (e.g., biotin and digoxigenin), which bind to antiligands or antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation.

The probes and primers necessary for practicing the present invention can be synthesized and labeled using well known techniques. Oligonucleotides used as probes and primers may be chemically synthesized according to the solid phase phosphoramidite triester method first described by Beaucage and Caruthers, *Tetrahedron Letts.*, 22:1859-1862, 1981, using an automated synthesizer, as described in Needham-VanDevanter et al., *Nucleic Acids Res.* 12:6159-6168, 1984. Purification of oligonucleotides is by either native acrylamide gel electrophoresis or by anion-exchange HPLC as described in Pearson and Regnier, *J. Chrom.*, 255: 137-149, 1983.

C. Detection of Methylation in ADAMTS9 Genomic Sequence

Methylation status of a segment of ADAMTS9 genomic sequence containing one or more CpG (cytosine-guanine dinucleotide) pairs is investigated to provide indication as to whether a test subject is suffering from gastric cancer, whether the subject is at risk of developing gastric cancer, or whether the subject's gastric cancer is worsening or improving.

Typically a segment of the ADAMTS9 genomic sequence that includes the 5' untranslated region (such as the promoter region) and includes one or more CpG nucleotide pairs is analyzed for methylation pattern. For example, SEQ ID NO:1, 6 or 7 or a portion thereof can be used to determine how many of the CpG pairs within the sequence are methylated and how many are not methylated. The sequence being analyzed should be long enough to contain at least 1 CpG dinucleotide pair and detection of methylation at this CpG site is typically adequate indication of the presence of gastric cancer cells. The length of the sequence being analyzed is usually at least 15 or 20 contiguous nucleotides, and may be longer with at least 25, 30, 50, 100, 200, 300, 400, or more contiguous nucleotides. At least one, typically 2 or more, often 3, 4, 5, 6, 7, 8, 9, or more, CpG nucleotide pairs are present within the sequence. In the cases of multiple (2 or more) CpG sites are analyzed for methylation status, when at least 50% of the CpG pairs within the analyzed genomic sequence are shown to be methylated, subject being tested is deemed to have gastric cancer or have an elevated risk of developing gastric cancer. As an example, SEQ ID NO:1, a segment of ADAMTS9 genomic sequence, SEQ ID NO:6, another segment of ADAMTS9 genomic, and SEQ ID NO:7, yet another segment of ADAMTS9 genomic, contain several CpG pairs. Some or majority of the CpG pairs in this region are found to be methylated in established gastric cancer cell lines and samples taken from gastric cancer, whereas non-cancerous stomach epithelial cells showed very few, if any at all, methylated CpG sites. For the purpose of determining the methylation pattern of a ADAMTS9 genomic sequence, bisulfite treatment followed by DNA sequencing is particularly useful, since bisulfite converts an unmethylated cytosine (C) to a uracil (U) while leaving methylated cytosines unchanged, allowing immediate identification through a DNA sequencing process. Optionally, an amplification process such as PCR is included after the bisulfite conversion and before the DNA sequencing.

1. DNA Extraction and Treatment

Methods for extracting DNA from a biological sample are well known and routinely practiced in the art of molecular biology, see, e.g., Sambrook and Russell, supra. RNA contamination should be eliminated to avoid interference with DNA analysis. The DNA is then treated with a reagent capable of modifying DNA in a methylation differential manner, i.e., different and distinguishable chemical structures will result from a methylated cytosine (C) residue and an unmethylated C residue following the treatment. Typically, such a reagent reacts with the unmethylated C residue(s) in a DNA molecule and converts each unmethylated C residue to a uracil (U) residue, whereas the methylated C residues remain unchanged. This unmethylated C→U conversion allows detection and comparison of methylation status based on changes in the primary sequence of the nucleic acid. An exemplary reagent suitable for this purpose is bisulfite, such as sodium bisulfite. Methods for using bisulfite for chemical modification of DNA are well known in the art (see, e.g., Herman et al., *Proc. Natl. Acad. Sci. USA* 93:9821-9826, 1996).

As a skilled artisan will recognize, any other reagents that are unnamed here but have the same property of chemically (or through any other mechanism) modifying methylated and unmethylated DNA differentially can be used for practicing the present invention. For instance, methylation-specific modification of DNA may also be accomplished by methylation-sensitive restriction enzymes, some of which typically cleave an unmethylated DNA fragment but not a methylated DNA fragment, while others (e.g., methylation-dependent endonuclease McrBC) cleave DNA containing methylated cytosines but not unmethylated DNA. In addition, a combination of chemical modification and restriction enzyme treatment, e.g., combined bisulfite restriction analysis (COBRA) (Xiong et al. 1997 *Nucleic Acids Res.* 25(12): 2532-2534), is useful for practicing the present invention. Other available methods for detecting DNA methylation include, for example, methylation-sensitive restriction endonucleases (MSREs) assay by either Southern blot or PCR analysis, methylation specific or methylation sensitive-PCR (MSP), methylation-sensitive single nucleotide primer extension (Ms-SnuPE), high resolution melting (HRM) analysis, bisulifte sequencing, pyrosequencing, methylation-specific single-strand conformation analysis (MS-SSCA), methylation-specific denaturing gradient gel electrophoresis (MS-DGGE), methylation-specific melting curve analysis (MS-MCA), methylation-specific denaturing high-performance liquid chromatography (MS-DHPLC), methylation-specific microarray (MSO). These assays can be either PCR analysis, quantitative analysis with fluorescence labelling or Southern blot analysis. Exemplary methylation sensitive DNA cleaving reagent such as restriction enzymes include AatII, AciI, AclI, AgeI, AscI, Asp718, AvaI, BbrP1, BceAI, BmgBI, BsaAI, BsaHI, BsiEI, BsiWI, BsmBI, BspDI, BsrFI, BssHII, BstBI, BstUI, ClaI, EagI, EagI-HF™, FauI, FseI, FspI, HaeII, HgaI, HhaI, HinP1I, HpaII, Hpy99I, HpyCH4IV, KasI, MluI, NarI, NgoMIV, NotI, NotI-HF™, NruI, Nt.BsmAI, PaeR7I, PspXI, PvuI, RsrII, SacII, SalI, SalI-HF™, SfoI, SgrAI, SmaI, SnaBI or TspMI. A methylation sensitive DNA cleaving reagent includes an enzyme that preferentially cleaves methylated DNA (e.g., MspJI) and an enzyme that preferentially cleaves unmethylated DNA (e.g., HpaII).

2. Optional Amplification and Sequence Analysis

Following the modification of DNA in a methylation-differential manner, the treated DNA is then subjected to sequence-based analysis, such that the methylation status of the ADAMTS9 genomic sequence may be determined. An amplification reaction is optional prior to the sequence analysis after methylation specific modification. A variety of polynucleotide amplification methods are well established and frequently used in research. For instance, the general methods of polymerase chain reaction (PCR) for polynucleotide sequence amplification are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

Although PCR amplification is typically used in practicing the present invention, one of skill in the art will recognize that amplification of the relevant genomic sequence may be accomplished by any known method, such as the ligase chain reaction (LCR), transcription-mediated amplification, and self-sustained sequence replication or nucleic acid sequence-based amplification (NASBA), each of which provides sufficient amplification.

Techniques for polynucleotide sequence determination are also well established and widely practiced in the relevant research field. For instance, the basic principles and general techniques for polynucleotide sequencing are described in various research reports and treatises on molecular biology and recombinant genetics, such as Wallace et al., supra; Sambrook and Russell, supra, and Ausubel et al., supra. DNA sequencing methods routinely practiced in research laboratories, either manual or automated, can be used for practicing the present invention. Additional means suitable for detecting changes (e.g., C→U) in a polynucleotide sequence for practicing the methods of the present invention include but are not limited to mass spectrometry, primer extension, polynucleotide hybridization, real-time PCR, melting curve analysis, high resolution melting analysis, heteroduplex analysis, pyrosequencing, and electrophoresis.

IV. Quantitation of Polypeptides

A. Obtaining Samples

The first step of practicing the present invention is to obtain a sample of stomach epithelium (e.g., stomach mucosa) from a subject being tested, assessed, or monitored for gastric cancer, the risk of developing gastric cancer, or the severity/progression of the condition. Samples of the same type should be taken from both a control group (normal individuals not suffering from any stomach disorder especially neoplasia) and a test group (subjects being tested for possible gastric cancer, for example). Standard procedures routinely employed in hospitals or clinics are typically followed for this purpose, as stated in the previous section.

For the purpose of detecting the presence of gastric cancer or assessing the risk of developing gastric cancer in test subjects, individual patients' stomach mucosa samples may be taken and the level of human ADAMTS9 protein may be measured and then compared to a standard control. If a decrease in the level of human ADAMTS9 protein is observed when compared to the control level, the test subject is deemed to have gastric cancer or have an elevated risk of developing the condition. For the purpose of monitoring disease progression or assessing therapeutic effectiveness in gastric cancer patients, individual patient's stomach epithelial samples may be taken at different time points, such that the level of human ADAMTS9 protein can be measured to provide information indicating the state of disease. For instance, when a patient's ADAMTS9 protein level shows a general trend of increase over time, the patient is deemed to be improving in the severity of gastric cancer or the therapy the patient has been receiving is deemed effective. A lack of change in a patient's ADAMTS9 protein level or a continuing trend of decrease on other hand would indicate a worsening of the condition and ineffectiveness of the therapy given to the patient. Generally, a lower ADAMTS9 protein level seen in a patient indicates a more severe form of the gastric cancer the patient is suffering from and a worse prognosis of the disease, as manifested in shorter life expectancy, higher rate of metastasis, resistance to therapy etc.

B. Preparing Samples for ADAMTS9 Protein Detection

The gastric (stomach) tissue sample from a subject is suitable for the present invention and can be obtained by well-known methods and as described in the previous section. In certain applications of this invention, stomach epithelial tissue (e.g., stomach mucosal tissue) may be the preferred sample type. In some instances, the gastric tissue sample is a gastric cancer sample containing a gastric cancer cell.

C. Determining the Level of Human ADAMTS9 Protein

A protein of any particular identity, such as ADAMTS9 protein, can be detected using a variety of immunological assays. In some embodiments, a sandwich assay can be performed by capturing the polypeptide from a test sample with an antibody having specific binding affinity for the polypeptide. The polypeptide then can be detected with a labeled antibody having specific binding affinity for it. Such immunological assays can be carried out using microfluidic devices such as microarray protein chips. A protein of interest (e.g., human ADAMTS9 protein) can also be detected by gel electrophoresis (such as 2-dimensional gel electrophoresis) and western blot analysis using specific antibodies. Alternatively, standard immunohistochemical techniques can be used to detect a given protein (e.g., human ADAMTS9 protein), using the appropriate antibodies. Both monoclonal and polyclonal antibodies (including antibody fragment with desired binding specificity) can be used for specific detection of the polypeptide. Such antibodies and their binding fragments with specific binding affinity to a particular protein (e.g., human ADAMTS9 protein) can be generated by known techniques.

Other methods may also be employed for measuring the level of ADAMTS9 protein in practicing the present invention. For instance, a variety of methods have been developed based on the mass spectrometry technology to rapidly and accurately quantify target proteins even in a large number of samples. These methods involve highly sophisticated equipment such as the triple quadrupole (triple Q) instrument using the multiple reaction monitoring (MRM) technique, matrix assisted laser desorption/ionization time-of-flight tandem mass spectrometer (MALDI TOF/TOF), an ion trap instrument using selective ion monitoring SIM) mode, and the electrospray ionization (ESI) based QTOP mass spectrometer. See, e.g., Pan et al., *J Proteome Res.* 2009 February; 8(2):787-797.

V. Establishing a Standard Control

In order to establish a standard control for practicing the method of this invention, a group of healthy persons free of any stomach disease (especially any form of tumor such as gastric cancer) as conventionally defined is first selected. These individuals are within the appropriate parameters, if applicable, for the purpose of screening for and/or monitoring gastric cancer using the methods of the present invention. Optionally, the individuals are of same gender, similar age, or similar ethnic background.

The healthy status of the selected individuals is confirmed by well established, routinely employed methods including but not limited to general physical examination of the individuals and general review of their medical history.

Furthermore, the selected group of healthy individuals must be of a reasonable size, such that the average amount/concentration of human ADAMTS9 mRNA or ADAMTS9 protein in the stomach tissue sample obtained from the group can be reasonably regarded as representative of the normal or average level among the general population of healthy people. Preferably, the selected group comprises at least 10 human subjects.

Once an average value for the ADAMTS9 mRNA or ADAMTS9 protein is established based on the individual values found in each subject of the selected healthy control group, this average or median or representative value or profile is considered a standard control. A standard deviation is also determined during the same process. In some cases, separate standard controls may be established for separately defined groups having distinct characteristics such as age, gender, or ethnic background.

VI. Treatment of Gastric Cancer

By illustrating the correlation of suppressed expression of ADAMTS9 protein and gastric cancer, the present invention further provides a means for treating patients suffering from gastric cancer: by way of increasing ADAMTS9 protein expression or biological activity. As used herein, treatment of gastric cancer encompasses reducing, reversing, lessening, or eliminating one or more of the symptoms of gastric cancer, as well as preventing or delaying the onset of one or more of the relevant symptoms.

A. Increasing ADAMTS9 Expression or Activity

1. Nucleic Acids Encoding ADAMTS9 Proteins

Enhancement of ADAMTS9 gene expression can be achieved through the use of nucleic acids encoding a functional ADAMTS9 protein. Such nucleic acids can be single-stranded nucleic acids (such as mRNA) or double-stranded nucleic acids (such as DNA) that can translate into an active form of ADAMTS9 protein under favorable conditions.

In one embodiment, the ADAMTS9-encoding nucleic acid is provided in the form of an expression cassette, typically recombinantly produced, having a promoter operably linked to the polynucleotide sequence encoding the ADAMTS9 protein. In some cases, the promoter is a universal promoter that directs gene expression in all or most tissue types; in other cases, the promoter is one that directs gene expression specifically in epithelial cells, especially in stomach epithelium. Administration of such nucleic acids can increase the ADAMTS9 protein expression in the target tissue, e.g., stomach epithelium. Since the human ADAMTS9 gene mRNA sequence is known as Genbank Accession No.: NM_182920 and provided herein as SEQ ID NO:3, one can derive a suitable ADAMTS9-encoding nucleic acid from the sequence, species homologs, and variants of these sequences.

2. ADAMTS9 Proteins

The human ADAMTS9 protein sequence is known as Genbank Accession No.: NP_891550 and provided herein as SEQ ID NO:5. By directly administering an effective amount of an active ADAMTS9 protein to a patient suffering from gastric cancer and exhibiting suppressed ADAMTS9 protein expression or activity, the disease may also be effectively treated. For example, this can be achieved by administering a recombinantly produced ADAMTS9 protein possessing its biological activity to the patient suffering from gastric cancer. Formulations and methods for delivering a protein- or polypeptide-based therapeutic agent are well known in the art.

3. Activators of ADAMTS9 Protein

Increased ADAMTS9 protein activity can be achieved with an agent that is capable of activating the expression of ADAMTS9 protein or enhancing the activity of ADAMTS9 protein. For example, a demethylating agent (e.g., 5-azacytidine or 5-azadeoxycytidine) may be able to activate ADAMTS9 gene expression by removing the suppression of ADAMTS9 gene expression caused by methylation of the promoter region of this gene. Other activating agents may include transcriptional activators specific for the ADAMTS9 promoter and/or enhancer. Such activating agents can be screened for and identified using the ADAMTS9 expression assays described in the examples herein.

Agonists of the ADAMTS9 protein, such as an activating antibody, are another kind of activators of the ADAMTS9 protein. Such activators act by enhancing the biological activity of the ADAMTS9 protein, typically (but not necessarily) by direct binding with the ADAMTS9 protein and/or its interacting proteins. Preliminary screening for such agonists may start with a binding assay for identifying molecules that physically interact with ADAMTS9 protein.

B. Pharmaceutical Compositions

1. Formulations

Compounds of the present invention are useful in the manufacture of a pharmaceutical composition or a medicament. A pharmaceutical composition or medicament can be administered to a subject for the treatment of gastric cancer.

Compounds used in the present invention, e.g., a ADAMTS9 protein, a nucleic acid encoding ADAMTS9 protein, or an activator of ADAMTS9 gene expression, are useful in the manufacture of a pharmaceutical composition or a medicament comprising an effective amount thereof in conjunction or mixture with excipients or carriers suitable for application.

An exemplary pharmaceutical composition for enhancing ADAMTS9 expression comprises (i) an express cassette comprising a polynucleotide sequence encoding a human ADAMTS9 protein as described herein, and (ii) a pharmaceutically acceptable excipient or carrier. The terms pharmaceutically-acceptable and physiologically-acceptable are used synonymously herein. The expression cassette may be provided in a therapeutically effective dose for use in a method for treatment as described herein.

An ADAMTS9 protein or a nucleic acid encoding an ADAMTS9 protein can be administered via liposomes, which serve to target the conjugates to a particular tissue, as well as increase the half-life of the composition. Liposomes include emulsions, foams, micelles, insoluble monolayers, liquid crystals, phospholipid dispersions, lamellar layers and the like. In these preparations the inhibitor to be delivered is incorporated as part of a liposome, alone or in conjunction with a molecule which binds to, e.g., a receptor prevalent among the targeted cells (e.g., skin cells), or with other therapeutic or immunogenic compositions. Thus, liposomes filled with a desired inhibitor of the invention can be directed to the site of treatment, where the liposomes then deliver the selected inhibitor compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al. (1980) *Ann. Rev. Biophys. Bioeng.* 9: 467, U.S. Pat. Nos. 4,235,871, 4,501,728 and 4,837,028.

Pharmaceutical compositions or medicaments for use in the present invention can be formulated by standard techniques using one or more physiologically acceptable carriers or excipients. Suitable pharmaceutical carriers are described herein and in "Remington's Pharmaceutical Sciences" by E. W. Martin. Compounds and agents of the present invention and their physiologically acceptable salts and solvates can be formulated for administration by any suitable route, including via inhalation, topically, nasally, orally, parenterally, or rectally.

Typical formulations for topical administration include creams, ointments, sprays, lotions, and patches. The pharmaceutical composition can, however, be formulated for any type of administration, e.g., intradermal, subdermal, intravenous, intramuscular, intranasal, intracerebral, intratracheal, intraarterial, intraperitoneal, intravesical, intrapleural, intracoronary or intratumoral injection, with a syringe or other devices. Formulation for administration by inhalation (e.g., aerosol), or for oral, rectal, or vaginal administration is also contemplated.

2. Routes of administration

Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Suitable formulations for transdermal application include an effective amount of a compound or agent of the present invention with carrier. Preferred carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used.

For oral administration, a pharmaceutical composition or a medicament can take the form of, for example, a tablet or a capsule prepared by conventional means with a pharmaceutically acceptable excipient. Preferred are tablets and gelatin capsules comprising the active ingredient, i.e., a ADAMTS9 protein or a nucleic acid encoding a ADAMTS9 protein, together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate, (b) lubricants, e.g., silica, talcum, stearic acid, its magnesium or calcium salt, metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners.

Tablets may be either film coated or enteric coated according to methods known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

Compounds and agents of the present invention can be formulated for parenteral administration by injection, for example by bolus injection or continuous infusion. Formulations for injection can be presented in unit dosage form, for example, in ampoules or in multi-dose containers, with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. Alternatively, the active ingredient can be in powder form for constitution with a suitable vehicle, for example, sterile pyrogen-free water, before use. In addition, they may also contain other therapeutically valuable substances. The compositions are prepared according to conventional mixing, granulating or coating methods, respectively, and contain about 0.1 to 75%, preferably about 1 to 50%, of the active ingredient.

For administration by inhalation, the active ingredient, e.g., a ADAMTS9 protein or a nucleic acid encoding a ADAMTS9 protein, may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

The inhibitors can also be formulated in rectal compositions, for example, suppositories or retention enemas, for example, containing conventional suppository bases, for example, cocoa butter or other glycerides.

Furthermore, the active ingredient can be formulated as a depot preparation. Such long-acting formulations can be administered by implantation (for example, subcutaneously or intramuscularly) or by intramuscular injection. Thus, for example, the active ingredient can be formulated with suitable polymeric or hydrophobic materials (for example as an emulsion in an acceptable oil) or ion exchange resins, or as sparingly soluble derivatives, for example, as a sparingly soluble salt.

A pharmaceutical composition or medicament of the present invention comprises (i) an effective amount of a compound as described herein that increases the level or activity of ADAMTS9 protein, and (ii) another therapeutic agent. When used with a compound of the present invention, such therapeutic agent may be used individually, sequentially, or in combination with one or more other such therapeutic agents (e.g., a first therapeutic agent, a second therapeutic agent, and a compound of the present invention). Administration may be by the same or different route of administration or together in the same pharmaceutical formulation.

3. Dosage

Pharmaceutical compositions or medicaments can be administered to a subject at a therapeutically effective dose to prevent, treat, or control gastric cancer as described herein. The pharmaceutical composition or medicament is administered to a subject in an amount sufficient to elicit an effective therapeutic response in the subject.

The dosage of active agents administered is dependent on the subject's body weight, age, individual condition, surface area or volume of the area to be treated and on the form of administration. The size of the dose also will be determined by the existence, nature, and extent of any adverse effects that accompany the administration of a particular compound in a particular subject. For example, each type of ADAMTS9 protein or nucleic acid encoding a ADAMTS9 protein will likely have a unique dosage. A unit dosage for oral administration to a mammal of about 50 to 70 kg may contain between about 5 and 500 mg of the active ingredient. Typically, a dosage of the active compounds of the present invention, is a dosage that is sufficient to achieve the desired effect. Optimal dosing schedules can be calculated from measurements of agent accumulation in the body of a subject. In general, dosage may be given once or more daily, weekly, or monthly. Persons of ordinary skill in the art can easily determine optimum dosages, dosing methodologies and repetition rates.

To achieve the desired therapeutic effect, compounds or agents may be administered for multiple days at the therapeutically effective daily dose. Thus, therapeutically effective administration of compounds to treat a pertinent condition or disease described herein in a subject requires periodic (e.g., daily) administration that continues for a period ranging from three days to two weeks or longer. Typically, agents will be administered for at least three consecutive days, often for at least five consecutive days, more often for at least ten, and sometimes for 20, 30, 40 or more consecutive days. While consecutive daily doses are a preferred route to achieve a therapeutically effective dose, a therapeutically beneficial effect can be achieved even if the agents are not administered daily, so long as the administration is repeated frequently enough to maintain a therapeutically effective concentration of the agents in the subject. For example, one can administer the agents every other day, every third day, or, if higher dose ranges are employed and tolerated by the subject, once a week.

Optimum dosages, toxicity, and therapeutic efficacy of such compounds or agents may vary depending on the relative potency of individual compounds or agents and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Agents that exhibit large therapeutic indices are preferred. While agents that exhibit toxic side effects can be used, care should be taken to design a delivery system that targets such agents to the site of affected tissue to minimize potential damage to normal cells and, thereby, reduce side effects.

The data obtained from, for example, cell culture assays and animal studies can be used to formulate a dosage range for use in humans. The dosage of such compounds lies preferably within a range of circulating concentrations that include the $ED_{50}$ with little or no toxicity. The dosage can vary within this range depending upon the dosage form employed and the route of administration. For any agents used in the methods of the invention, the therapeutically effective dose can be estimated initially from cell culture assays. A dose can be formulated in animal models to achieve a circulating plasma concentration range that includes the $IC_{50}$ (the concentration of the agent that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of agents is from about 1 ng/kg to 100 mg/kg for a typical subject.

Exemplary dosages for ADAMTS9 protein or a nucleic acid encoding a ADAMTS9 protein described herein are provided. Dosage for a ADAMTS9-encoding nucleic acid, such as an expression cassetter, can be between 0.1-0.5 mg/eye, with intravitreous administration (e.g., 5-30 mg/kg). Small organic compounds activators can be administered orally at between 5-1000 mg, or by intravenous infusion at between 10-500 mg/ml. Monoclonal antibody activators can be administered by intravenous injection or infusion at 50-500 mg/ml (over 120 minutes); 1-500 mg/kg (over 60 minutes); or 1-100 mg/kg (bolus) five times weekly. ADAMTS9 protein or peptide activators can be administered subcutaneously at 10-500 mg; 0.1-500 mg/kg intravenously twice daily, or about 50 mg once weekly, or 25 mg twice weekly.

Pharmaceutical compositions of the present invention can be administered alone or in combination with at least one additional therapeutic compound. Exemplary advantageous therapeutic compounds include systemic and topical anti-inflammatories, pain relievers, anti-histamines, anesthetic compounds, and the like. The additional therapeutic compound can be administered at the same time as, or even in the same composition with, main active ingredient (e.g., a ADAMTS9 protein or a nucleic acid encoding the protein). The additional therapeutic compound can also be administered separately, in a separate composition, or a different dosage form from the main active ingredient. Some doses of the main ingredient, such as a ADAMTS9 protein or a nucleic acid encoding a ADAMTS9 protein, can be administered at the same time as the additional therapeutic compound, while others are administered separately, depending on the particular symptoms and characteristics of the individual.

The dosage of a pharmaceutical composition of the invention can be adjusted throughout treatment, depending on severity of symptoms, frequency of recurrence, and physiological response to the therapeutic regimen. Those of skill in the art commonly engage in such adjustments in therapeutic regimen.

VII. Kits and Devices

The invention provides compositions and kits for practicing the methods described herein to assess the level of ADAMTS9 mRNA or ADAMTS9 protein in a subject, which can be used for various purposes such as detecting or diagnosing the presence of gastric cancer, determining the risk of developing gastric cancer, and monitoring the progression of gastric cancer in a patient.

Kits for carrying out assays for determining ADAMTS9 mRNA level typically include at least one oligonucleotide useful for specific hybridization with at least one segment of the ADAMTS9 coding sequence or its complementary sequence. Optionally, this oligonucleotide is labeled with a detectable moiety. In some cases, the kits may include at least two oligonucleotide primers that can be used in the amplification of at least one segment of ADAMTS9 DNA or mRNA by PCR, particularly by RT-PCR.

Kits for carrying out assays for determining ADAMTS9 protein level typically include at least one antibody useful for specific binding to the ADAMTS9 protein amino acid sequence. Optionally, this antibody is labeled with a detectable moiety. The antibody can be either a monoclonal antibody or a polyclonal antibody. In some cases, the kits may include at least two different antibodies, one for specific binding to the ADAMTS9 protein (i.e., the primary antibody) and the other for detection of the primary antibody (i.e., the secondary antibody), which is often attached to a detectable moiety.

Typically, the kits also include an appropriate standard control. The standard controls indicate the average value of ADAMTS9 protein or ADAMTS9 mRNA in the stomach epithelium of healthy subjects not suffering from gastric cancer. In some cases such standard control may be provided in the form of a set value. In addition, the kits of this invention may provide instruction manuals to guide users in analyzing test samples and assessing the presence, risk, or state of gastric cancer in a test subject.

In a further aspect, the present invention can also be embodied in a device or a system comprising one or more such devices, which is capable of carrying out all or some of the method steps described herein. For instance, in some cases, the device or system performs the following steps upon receiving a stomach tissue sample, e.g., a stomach mucosa sample taken from a subject being tested for detecting gastric cancer, assessing the risk of developing gastric cancer, or monitored for progression of the condition: (a) determining in sample the amount or concentration of ADAMTS9 mRNA, ADAMTS9 protein; (b) comparing the amount or concentration with a standard control value; and (c) providing an output indicating whether gastric cancer is present in the subject or whether the subject is at risk of developing gastric cancer, or whether there is a change, i.e., worsening or improvement, in the subject's gastric cancer condition. In other cases, the device or system of the invention performs the task of steps (b) and (c), after step (a) has been performed and the amount or concentration from (a) has been entered into the device. Preferably, the device or system is partially or fully automated.

EXAMPLES

The following examples are offered to illustrate, but not to limit the claimed invention. It should be understood that the examples and embodiments described herein are for illustrative purposes only and that various modifications or changes in light thereof will be suggested to persons skilled in the art and are to be included within the spirit and purview of this application.

Abstract

Gastric cancer is a major cause of cancer-related death worldwide. Inactivation of tumor-related genes through hypermethylation of CpG islands in the promoter region plays an important role in the development of various cancers. This study identifies a novel preferentially methylated gene, a disintegrin-like and metalloprotease with thrombospondin type 1 motif 9 (ADAMTS9). In particular, it was determined that ADAMTS9 promoter methylation is associated with poor survival in gastric cancer. ADAMTS9 also acts a functional tumor suppressor through inhibiting the AKT/mTOR pathway in cancers such as gastric cancer.

Materials and Methods
1. Human Gastric Specimens
   a. Tissue Samples

Gastric biopsy specimens were obtained from gastric cancer patients during endoscopy before any therapeutic intervention. The biopsy specimens were snap-frozen in liquid nitrogen and stored at −80° C. for molecular analyses. A total of 83 patients with confirmed gastric normal tissues were examined. Tumor was staged according to the TNM staging system. *H. pylori* infection was defined by the presence of the gram-negative curved bacilli on histology. All histological assessments were made by an experienced pathologist. Patients were being followed up regularly in our clinic and the median follow-up duration since the time of diagnosis was 16.8 months. Data for *H pylori* infection status, Lauren classification, and TNM stage/survival time were missing in 31, 19, and 11 patients, respectively. All patients were treated according to a standard protocol with surgery being the mainstay of treatment. All patients and controls gave informed consent, and the study protocol was approved by the Clinical Research Ethics Committee of the Chinese University of Hong Kong.

b. Tumor Cell Line

Eight gastric cancer cell lines (BGC823, MGC803, AGS, MKN28, MKN45, SNU719, YCC 10 and Kato III) were obtained from the American Type Culture Collection (Manassas, Va.) and human non-tumorigenic gastric epithelial cell line GES-1 was obtained from Cancer Research Institute of Beijing, Beijing University, China. They were cultured in Dulbecco's modified Eagle's medium (DMEM) medium or RPMI 1640 medium (Gibco BRL, Rockville, Md.) supplemented with 10% fetal bovine serum and incubated in 5% $CO_2$ at 37° C.

2. Bioinformatic Analysis of ADAMTS9 Gene

The online database of University of California Santa Cruz Genome Bioinformatics (UCSC) was used to obtain the related information about ADAMTS9 gene. CpG islands in the ADAMTS9 gene promoter region were predicted by CpG Island Searcher (Takai et al., *In Silico Biol,* 2003, 3(3):235-240). CpG islands are defined as DNA region greater than 500 bp with GC content above 55% and an observed/expected CpG ratio above 0.65 (Takai et al., supra).

3. Gene Expression Analysis
   a. RNA Isolation

Total RNA was isolated using Quizol reagent (Qiagen, Valencia, Calif., USA). first, about $5-10 \times 10^6$ cells or 30 mg tissue was homogenized in 1 mL Qiazol reagent and incubated at room temperature for 10 min. For each sample, 0.2 mL chloroform was added. The mixture should be shaken vigorously for 15 sec and placed at room temperature for another 3 min. Samples were centrifuged at 12,000 g for 20 min at 4° C. and separated into two layers. The upper aqueous phase containing RNA was transferred to a new tube, mixed with 0.7 ml isopropanol, incubated at room temperature for 10 min and then centrifuged at 12,000 g for 10 min at 4° C. After discarding the supernatant, the RNA pellet was washed twice with 1 mL 75% ethanol; air dried for 5 min and re-dissolved the RNA with RNase-free $H_2O$. Contamination of DNA was eliminated by the RNase-free DNaseI digestion (GE Healthcare, Buckinghamshire, England). The quality and quantity of total RNA were determined by measuring absorbance at 260 nm/280 nm using NanoDrop ND-1000 (NanoDrop Technologies, Wilmington, Del., USA). The purified RNA was store at −80° C. until use.

b. cDNA Synthesis

MultiScribe Reverse Transcriptase Kit (Applied Biosystems, Foster City, Calif., USA) was used to synthesize cDNA. The reaction mixture contained 1× Reverse Transcriptase buffer, 1×dNTP, 1× random primer (supplied by kit), 2.5 U/μL reverse transcriptase, 1 U/μL RNase inhibitor and 2 μg total RNA. The mixture was incubated at 25° C. for 10 min, then 37° C. for 120 min, then 85° C. for 5 min to inactivate the enzymes. The cDNA was stored at −80° C. until other application.

c. Semiquantitative Reverse Transcription PCR (RT-PCR)

Semiquantitative RT-PCR was performed in a total volume of 25 μL reaction containing GeneAmp 1×PCR Buffer II (Applied Biosystems), 2.5 mM $MgCl_2$, 200 μM each of dNTP, 200 nM each of primers, 0.5 U of AmpliTaq Gold DNA polymerase (Applied Biosystems) and 30-50 ng cDNA. The PCR program started with an initial denaturation at 95° C. for 10 min, followed by 32-35 cycles (94° C. for 30 sec, 58° C. for 30 sec, and 72° C. for 30 sec) of amplification, with a final extension at 72° C. for 10 min. The PCR reaction were analyzed by gel electrophoresis. The expression of the target gene was normalized by the expression of housekeeping gene β-actin, which served as an internal control. All primers used to amplify the transcripts are listed in Table 1.

TABLE 1

List of primers for ADAMTS9

| Primer Name | Sequence (5'-3') | SEQ ID NO |
|---|---|---|
| RT-PCR primers for detecting ADAMTS9 mRNA expression | | |
| ADAMTS9-F | CAATACCAACTCCGAGCACA | SEQ ID NO: 8 |
| ADAMTS9-R | TGGGGTTTGTTTTGTTCCTC | SEQ ID NO: 9 |
| BGS primers | | |
| ADAMTS9-BGS-F | GGGGTATTTGAGAGGTTGTGGATT | SEQ ID NO: 10 |
| ADAMTS9-BGS-R | CTACATAATACTTCCCACCCCTC | SEQ ID NO: 11 |
| MSP primers | | |
| ADAMTS9-MSP-MF | TTTTTCGTTTTTTTTGTTCGTTC | SEQ ID NO: 12 |
| ADAMTS9-MSP-MR | AAACTAAACCGCTCGAACCG | SEQ ID NO: 13 |
| ADAMTS9-MSP-UF | GTTTTTTGTTTTTTTTGTTTGTTT | SEQ ID NO: 14 |
| ADAMTS9-MSP-UR | AAAAACTAAACCACTCAAACCA | SEQ ID NO: 15 | d. Protein Extraction

Protein was prepared by using CytoBuster Protein Extraction Reagent (Merck Chemicals, Nottingham, UK). The cells were pelleted at 3000 g for 10 min. The pellet was then resuspended in CytoBuster using 100 μL per $10^6$ cells. The mixture was incubated at room temperature for 5 min. Next, the tube was centrifuged for 10 min at 4° C. at 15,000 g and the supernatant was transferred to a fresh tube.

e. Sodium Dodecyl Sulfate Polyacrylamide Gel Electrophoresis (SDS-PAGE) and Western Blot Forty micrograms of protein were separated by 5% upper gel and 10% lower gel. After SDS-PAGE, the protein was transfer to an equilibrated polyvinylidene difluoride (PVDF) membrane (Amersham Biosciences, Buckinghamshire, UK) by semi-dry machine at 15 V for 40 min. The membrane was blocked in 5% non-fat milk dissolved by TBS/T solution (Tris-buffered saline (Invitrogen) and 0.1% Tween 20 (Sigma-Aldrich)) at room temperature for 1 hr with shaking After blocking, the membrane was incubated in primary antibody diluted in 5% non-fat milk at 4° C. overnight with shaking. After incubation with the secondary antibody at room temperature for 1 hr, the proteins were detected by enhanced chemiluminescence (ECL, Amersham Corporation, Arlington. Heights, Ill., USA).

4. Gene Expression Analysis a. Genomic DNA Extraction

Genomic DNA from GC cell lines and tissue samples were isolated by using DNA mini kit (Qiagen) according to the kit protocol. About 25 mg samples were lysed in 180 μL of QIAamp ATL buffer and 20 μL of proteinase K in a 1.5 mL microcentrifuge tubes for 1 hour at 56° C. Four microliter of RNase A (100 mg/ml, QIAgen) was added and mixed by pulse-vortexing for 15 s followed by 2 min incubation at room temperature. Then 200 μL of AL buffer was added to the lysate and samples were incubated for 10 min at 70° C. After adding 200 μL of absolute ethanol, the solution was mixed by pulse-vortexing for 15 seconds. Then lysates were purified over a QIAamp column as specified by the manufacturer. The genomic DNA was diluted in 200 μL DNase-free $H_2O$. The quality and quantity of DNA were determined by measuring absorbance at 260 nm/280 nm using NanoDrop ND-1000 (NanoDrop).

b. Sodium Bisulfite Conversion

The genomic DNA was modified by sodium metabisulfite as described in, e.g., Tao et al., *Hum. Mol. Genet.*, 2002, 11(18):2091-102. Briefly, 5 μg genomic DNA in 30 μL TE buffer (Sigma-Aldrich) was mixed with 3.3 μL of 3 mM NaOH to a final concentration of 0.3 mM and incubated at 37° C. for 15 min. Denatured DNA was mixed with 333 μL of bisulfite solution and treated in the dark for 4 hr at 55° C. The bisulfite solution was prepared as 2.4 M sodium metabisulfite (pH 5.0-5.2) (Sigma-Aldrich) and 0.5 mM hydroquinone (Sigma-Aldrich). The treated DNA was desalted and purified using the Qiaex II kit (Qiagen) according to the manufacturer's protocol. DNA was then treated with 0.3 M NaOH at 37° C. for 15 min and precipitated with 3 M ammonium acetate and 3 volumes of ethanol. Recovered DNA was dissolved in 100 μL TE buffer (pH 8.0) and stored at −20° C.

c. Demethylation Treatment Using 5-Aza-2'-Deoxycytidine (5-Aza)

Cells were seeded at a density of $1 \times 10^5$/100-mm dishes and grew for 24 hr. Cells were then treated with 2 μM 5-aza-2'-deoxycytidine (5-Aza) (Sigma-Aldrich) for 5 days. The 5-Aza was replenished every day. The gene expression of ADAMTS9 was evaluated using semiquantitative RT-PCR, as described above.

d. Methylation Specific PCR (MSP)

Methylation specific and unmethylation specific primers were designed to assess methylation status in the GC cell lines. The mixture for PCR contained 1×PCR Buffer II (Applied Biosystems), 2 mM $MgCl_2$, 200 μM each of dNTP, 600 nM each of primers, 0.5 U of AmpliTaq Gold DNA polymerase (Applied Biosystems) and 20 ng bisulfite treated DNA. The PCR program was 95° C. for 10 min, followed by 38 cycles (94° C. for 30 sec, 60° C. for 30 sec, and 72° C. for 30 sec) of amplification, with a final extension at 72° C. for 5 min. PCR products were evaluated by gel electrophoresis analysis. Detailed description of MSP is found in, e.g., Herman et al., *Proc. Natl. Acad, Sci. USA*, 1996, 93:9821-9826.

e. Bisulfite Genomic Sequencing (BGS)

Bisulfite treated DNA was amplified using primers listed in Table 1. PCR amplification with 2 μL of bisulfite-treated DNA gives a PCR product of about 425 bp, containing 25 CpG dinucleotides at the ADMTS9 promoter region. Amplified BGS products were sequenced. Sequencing analysis was performed by SeqScape software (Applied Biosystems, Foster City, Calif.).

5. Biological Function Analysis a. Colony Formation Assay

AGS and BGC823 cells transfected with pCEP4-ADAMTS9-expressing or pCEP4 empty vector were selected with Hygromycin B (Invitrogen, Carlsbad, Calif.) for 2 weeks. Then cells were fixed with 70% ethanol for 10 min and stained with 0.5% crystal violet solution for 10 min. Colony with more than 50 cells per colony was counted. The experiment was conducted in three independent triplicates.

b. Cell Viability Assay

MTS assay, which is the short form of 3-(4,5-dimethylthiazol-2-yl)-5-(3-carboxymethoxyphenyl)-2-(4-sulfophenyl)-2H-tetrazolium assay, was performed using CellTiter 96 $AQ_{ueous}$ One Solution Cell Proliferation Assay kit (Promega). AGS and BGC823 cells ($5 \times 10^3$ per well) were seeded in 96-well plates and transient transfected with pCMV-ADAMTS9 vector or pCMV empty vector. The plate was incubated at 37° C. in a 5% $CO_2$ incubator. After 48 hr, 20 μL MTS reagent was added into the culture medium. The culture was incubated at 37° C. in a $CO_2$ incubator for 30 min to 2 hr. Absorbance of the samples was measured at 490 nm 48 hr post transfection. The experiment was replicated three times.

c. Annexin V Apoptosis Assay

Annexin V is a protein which could bind the cell membrane after apoptosis have occurred and before membrane integrity has been lost. The proportion of apoptotic cells was evaluated using Annexin V and 7-amino-actinomycin (7-AAD) double staining Briefly, pCMV-ADAMTS9 or empty vector-transfected cells were harvested at 48 h post-transfection pCMV-ADAMTS9 vector or pCMV empty vector. The cells washed with 1×PBS was resuspended in 100 µL ice-cold annexin-binding buffer (10 mM HEPES, 140 mM NaCl and 2.5 mM $CaCl_2$, pH 7.4) containing 5 µL Annexin V conjugated with Alexa Fluor 488 (Invitrogen) and 2 µL 7-AAD staining After incubation for 15 min at room temperature, cells were mixed with additional 400 µL of ice-cold annexin-binding buffer and analyzed using flow cytometry.

d. Tube Formation Assay

Conditioned media were collected by incubating pCMV-ADAMTS9 and pCMV vector-alone transfected cells (BGC823 and AGS) without serum for 24 hours. After Matrigel (Milipore, Billerica, Mass.) thawed on ice, the 96-well plate was coated with 50 µL Matrigel each well and incubated at 37° C. for 30 min to allow the Matrigel to polymerize. A total of $1 \times 10^4$ HUVEC cells were seeded into each well and incubated with 100 µL conditioned media from ADAMTS9 and vector-alone transfectants plus 1% fetal bovine serum. Cells were then incubated for 4 hours to allow formation of tube-like structures. Image analysis of tube length was carried out using Image software from the NIH website.

e. In Vivo Tumorigenicity

BGC823 cells ($5 \times 10^5$ cells in 0.2 mL phosphate-buffered saline) transfected with pCMV-ADAMTS9 vector or pCMV empty vector were injected subcutaneously into the dorsal flank of 5-week-old male Balb/c nude mice, separately. Tumor diameter was measured every 3 days for 15 days. Tumor volume ($mm^3$) was estimated by measuring the longest and shortest diameter of the tumor and calculating as follows: volume=(shortest diameter)$^2 \times$(longest diameter)$\times$ 0.5. All experimental procedures were approved by the Animal Ethics Committee of the Chinese University of Hong Kong.

6. Statistical Analysis

Data were expressed as mean±standard (SD) deviation. The difference in tumor growth rate between the 2 groups of mice was determined by repeated-measures analysis of variance. The chi-square test was used for comparison of patient characteristics and distributions of methylation by vital status. Patient age (at entry or follow-up evaluation) by vital status was compared using the t test. Relative risks (RRs) of death associated with ADAMTS9 methylation and other predictor variables were estimated from univariate Cox proportional hazards model. Multivariate Cox models also were constructed to estimate the RR for ADAMTS9 methylation. Overall survival in relation to methylation status was evaluated by the Kaplan-Meier survival curve and the log-rank test. All analyses were performed using SPSS for Windows 11.0.1 software. P<0.05 was considered statistically significant.

Results

1. Data Mining for ADAMTS9 Gene a. ADAMTS9

ADAMTS9 is a member of the ADAMTS (a disintegrin and metalloproteinase with thrombospondin motifs) protein family and have been implicated in the cleavage of proteoglycans, the control of organ shape during development, and the inhibition of angiogenesis. Using University of California Santa Cruz Genome Bioinformatics (UCSC) database, the ADAMTS9 gene was localized to chromosome 3p14.3-p14.2. ADAMTS9 encodes a metalloproteinase which has 1935 amino acids.

b. ADAMTS9 CpG Island

MSP primers and BGS primers were designed according to CpG island analysis results (FIG. 1 and Table 1). FIG. 1 shows part (segment) of the promoter region and the first exon of ADAMTS9. The transcription starting site is marked as "TSS". The BGS region and the 24 CpG sites within the BGS region are also represented in FIG. 1.

Figure 2:
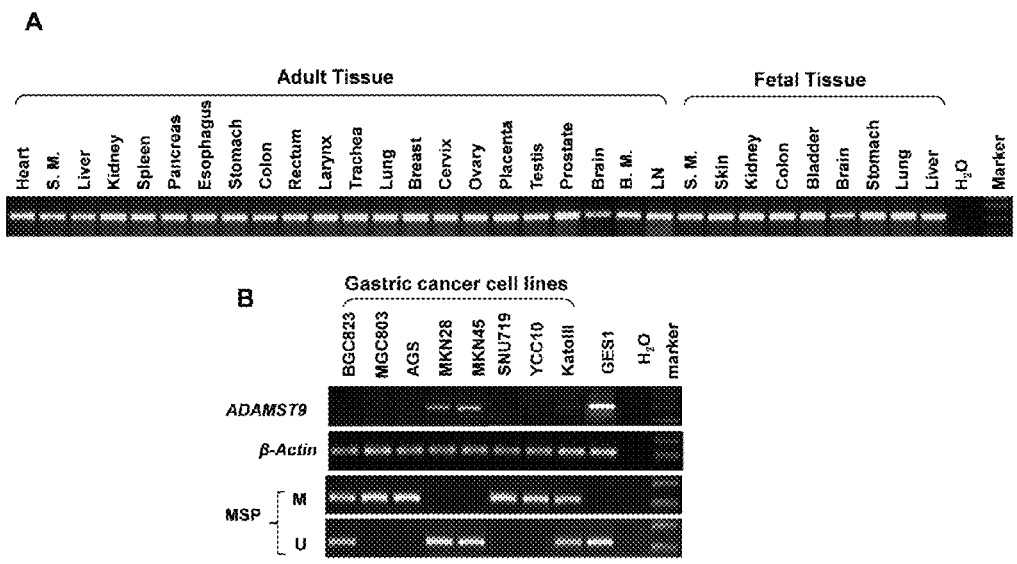
FIG. 2 shows ADAMTS9 mRNA expression and methylation status in adult tissue (A), fetal tissue (A), and cell lines (B). Transcriptional silencing of ADAMTS9 by methylation was detected in gastric cancer cell lines.

2. ADAMTS9 Gene Expression a. ADAMTS9 was Epigenetically Suppressed in Cancer Cell Lines FIG. 2 shows that ADAMTS9 was expressed in all normal adult tissues and fetal tissues examined, as well as in a normal human gastric epithelial cell line (GES1). However, ADAMTS9 was silenced or downregulated in 6 out of 8 (75%) gastric cancer cell lines. The role of promoter methylation in silencing ADAMTS9 was evaluated by MSP (M: bands amplified by methylation primers, U: bands amplified by unmethylation primers). Full or partial methylation was detected in 6 gastric cancer cell lines (BGC823, MGC803, AGS, SNU719, YCC10, and KatoIII), which showed silenced or down-regulated ADAMTS9 expression, whereas methylation was not detected in the cell lines (MKN28 and MKN45) with ADAMTS9 expression (FIG. 2B).

Figure 3:
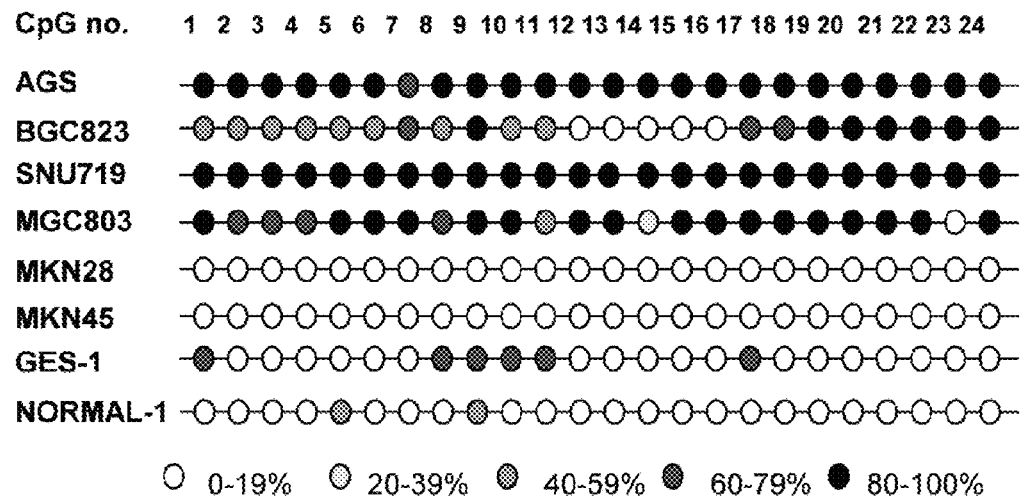
FIG. 3 shows the methylation status of ADAMTS9 in GC cell lines by bisulfite genomic sequencing (BGS).

The methylation density within the ADAMTS9 promoter region was then characterized and validated by high-resolution BGS. The BGS results were consistent with those of MSP in which dense methylation was found in methylated cell lines (AGS, BGC823, SNU719, MGC803), but not in unmethylated MKN28, MKN45 and normal gastric tissues (FIG. 3).

b. ADAMTS9 Expression was Restored after Demethylation Treatment

Figure 4:
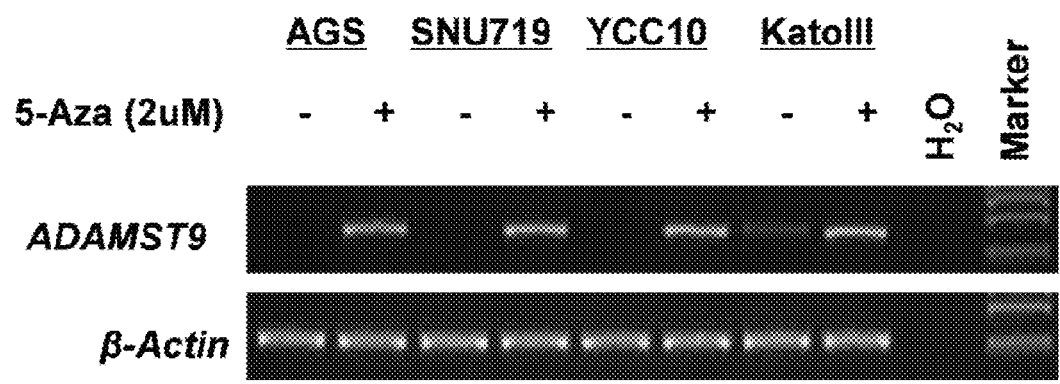
FIG. 4 shows the effect of a demethylating agent (5-Aza) on ADAMTS9 expression on cell lines. Expression was restored after treatment with the agent.

To confirm whether promoter methylation mediated ADAMTS9 silencing, four methylated cell lines that showed silencing of ADAMTS9 were treated with the demethylation agent 5-Aza. This treatment restored ADAMTS9 expression in all of them (FIG. 4), indicating that promoter methylation was associated with the transcriptional silence of ADAMTS9 in gastric cancer cells.

3. Functional Assay a. Inhibition of Cell Proliferation by ADAMTS9

Figure 5:
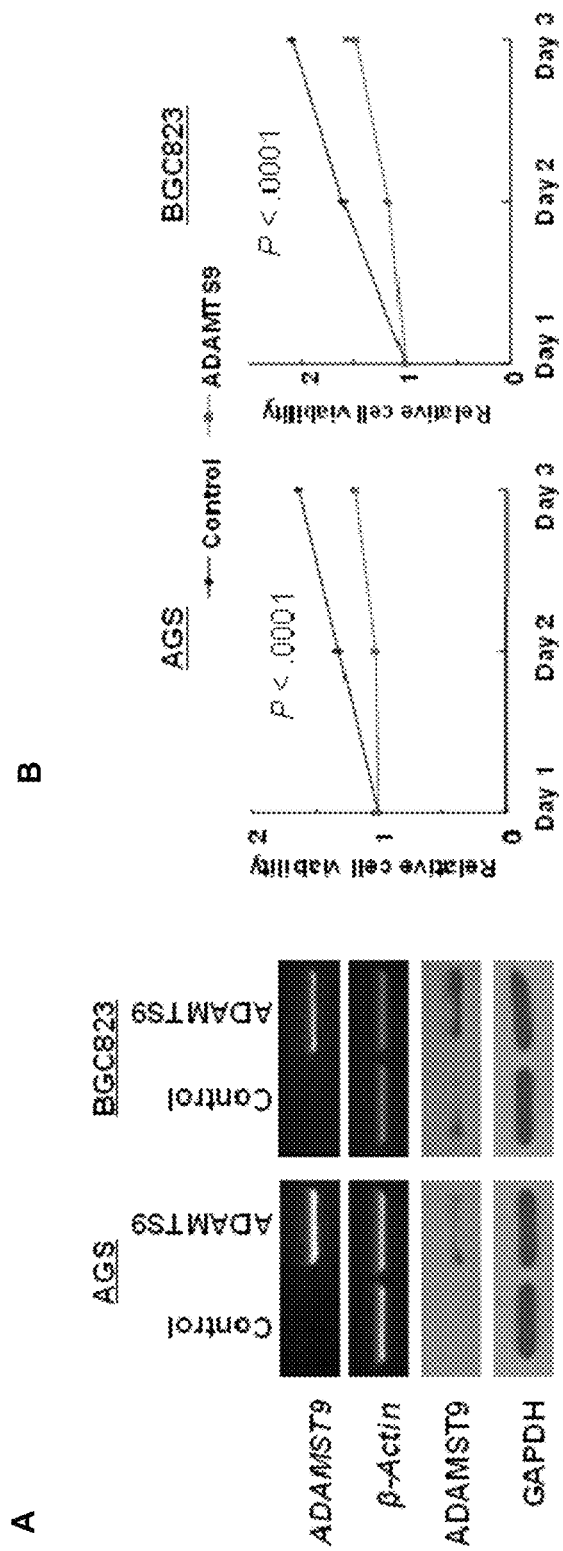
FIG. 5 shows exogenous ADAMTS9 expression (e.g., nucleic acid expression and protein expression) (A) and cell viability (B) in cell lines.
Figure 6:
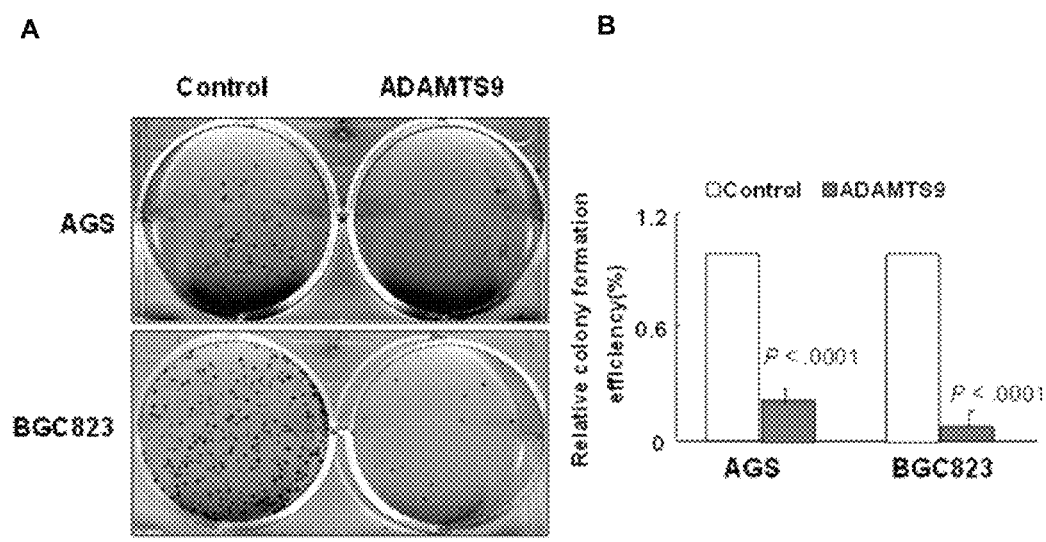
FIG. 6 shows the effect of ADAMTS9 expression on transfected cells in a colony formation assay (A). ADAMTS9 inhibits gastric cancer cell growth (B).

In vitro biological effects of ADAMTS9 on cell growth in the ADAMTS9 non-expressing cell lines (AGS and BGC823) were examined by cell viability assay and colony formation assay. MTS assay was used for measuring the cell viability. Ectopic expression of ADAMTS9 in these GC cell lines caused a significant decrease in cell viability (FIG. 5). The inhibitory effect on GC cell growth was further confirmed by colony formation assay. The colonies formed in ADAMTS9-transfected cells were significantly lesser and smaller in size than in empty vector-transfected cells (FIG. 6). Both colony formation and MTS assay solidly demonstrated that ADAMTS9 could inhibit cell growth of GC cells in vitro.

b. Induction of Cell Apoptosis by ADAMTS9

Figure 7:
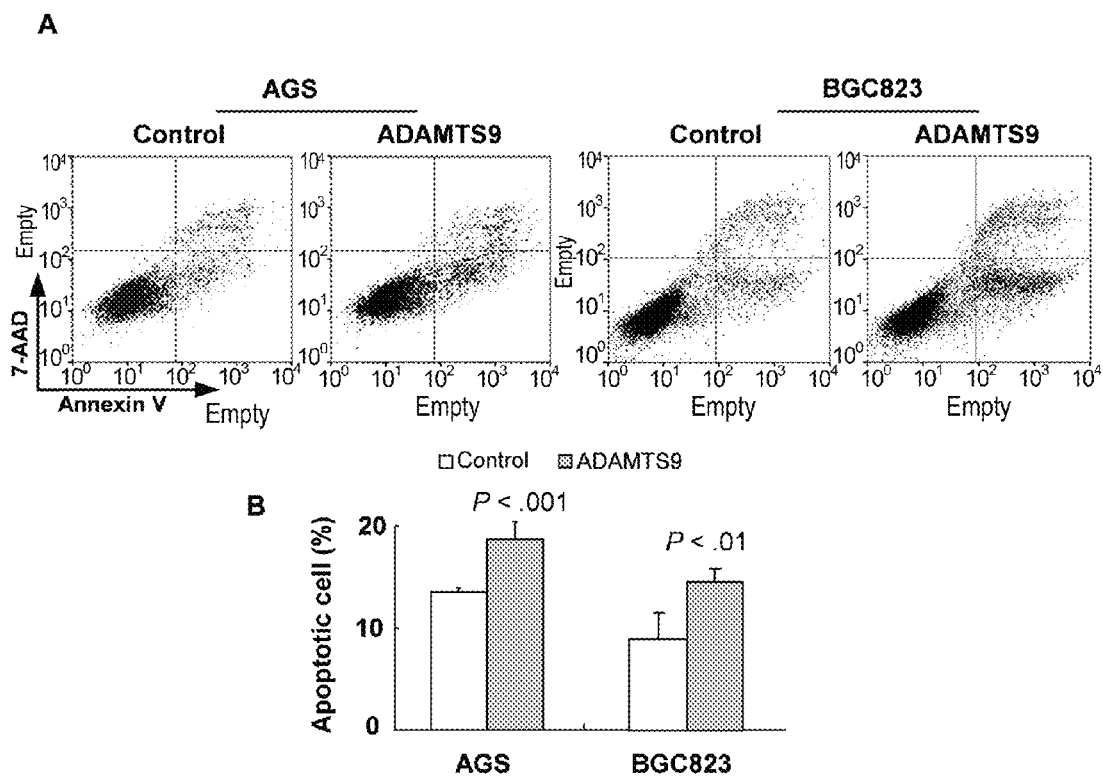
FIG. 7 shows the pro-apoptotic effect of ADAMTS9 expression on transfected cells (A). Data indicates that ADAMTS9 induces apoptosis (B).

To examine the contribution of apoptosis to the observed growth suppression by ADAMTS9, cell apoptosis was evaluated using Annexin V-APC and 7-AAD double staining Ectopic expression of ADAMTS9 resulted in a significant increase in apoptotic cells as compared with vector control both in AGS (P<0.001) and in BGC823 (P<0.01) cells (FIG. 7).

c. Inhibition of Angiogenesis by ADAMTS9

Figure 8:
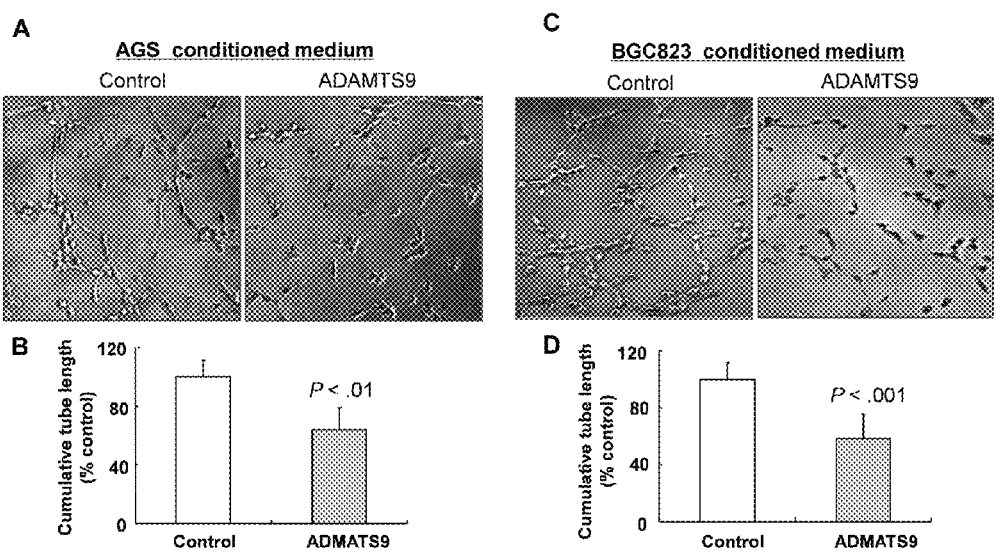
FIG. 8 shows the anti-angiogenesis effect of ADAMTS9 expression on transfected cells (A and C). In vitro angiogenesis was reduced in cells ectopically expressing ADAMTS9 (B and D).

Human umbilical vein endothelial cell (HUVEC) tube formation assay was performed to test the effect of ADAMTS9 on angiogenesis of gastric cancer cells in vitro. As shown in FIG. 8, conditioned culture medium from ADAMTS9 transfected AGS and BGC823 cells significantly reduced the tube-forming capacity of HUVEC on Matrigel.

d. In Vivo Tumor Suppression

Figure 9:
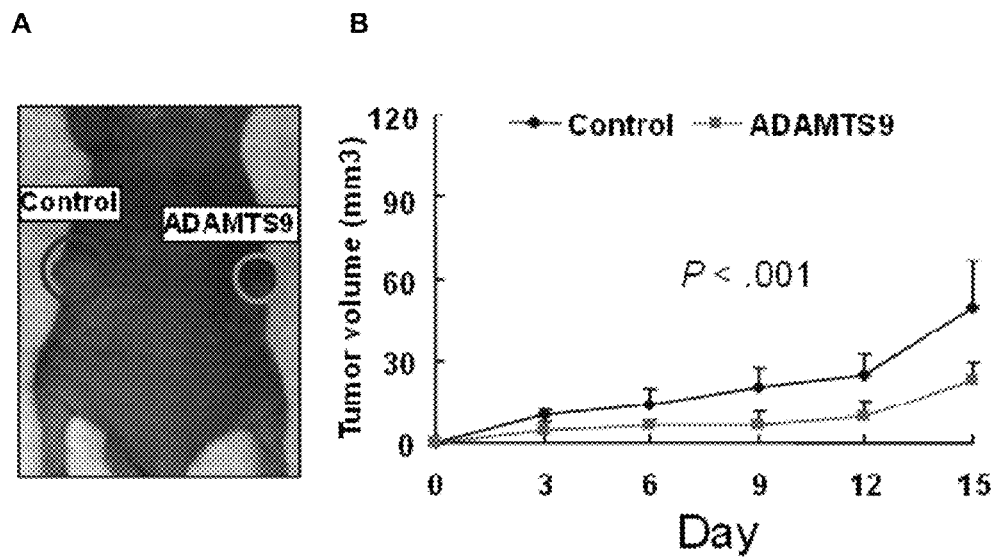
FIG. 9 shows the growth-inhibition effect of ADAMTS9 expression in nude mice (A and B).

The ability of ADAMTS9 to suppress the growth of gastric cancer cells in vivo was evaluated. The subcutaneous tumor growth of BGC823 transfected with ADAMTS9 or empty vector in nude mice is shown in FIG. 9. The tumor growth was significantly lower in ADAMTS9 transfected nude mice as compared with the vector control mice (P<0.001).

Figure 10:
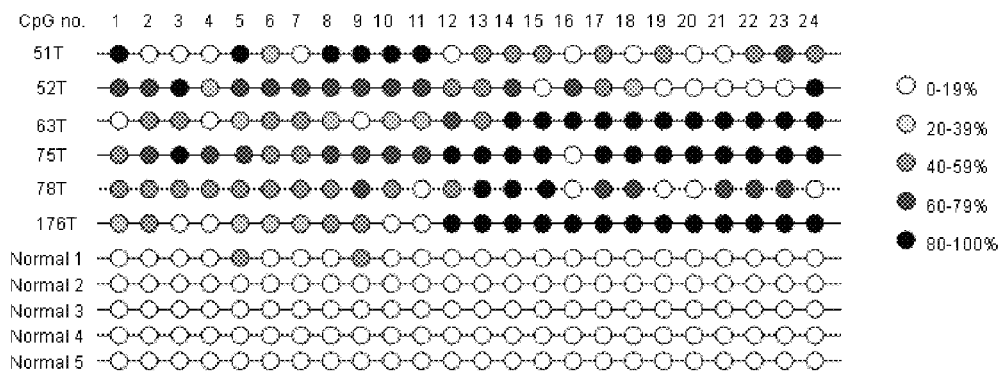
FIG. 10 shows the methylation status of ADAMTS9 in primary GC and normal gastric tissue samples.

4. Methylation Status of Gastric Cancer (GC) Patients a. Methylation Status in the GC Tissues and Normal Gastric Tissues The clinical application of ADAMTS9 methylation was evaluated in 83 primary gastric cancers and in 20 healthy gastric tissue samples. Among 83 gastric cancer cases, partial and dense promoter methylation of ADAMTS9 was detected in 27.7% (23/83) cases, but none in 20 healthy gastric tissue samples (FIG. 10).

b. Association Between ADAMTS9 Methylation and Clinical Characteristics

To evaluate the clinical application of ADAMTS9 in gastric tumors, the correlation between ADAMTS9 methylation and clinical features including patient age, gender, tumor stage, *H. pylori* infection status, Lauren type and tumor differentiation was analyzed. There was no correlation between ADAMTS9 methylation and clinicopathologic features such as age, gender, tumor location, tumor staging, histologic type, and pathological stage, except *H. pylori* infection (P<0.05).

In univariate Cox regression analysis, ADAMTS9 methylation in tumor tissues was associated with an increased risk of cancer-related death (RR, 1.936; 95% confidence interval, 1.123-3.337; P<0.017). In the multivariate model, after the adjustment for potential confounding factors, ADAMTS9 methylation in tumor tissues was found to predict poorer survival (RR, 2.788; 95% confidence interval, 1.474-5.274; P=0.002). Tumor TNM stage was another independent predictor for overall survival. Patients in stages I-III had a significantly better survival when compared with patients with a stage IV tumor.

Figure 11:
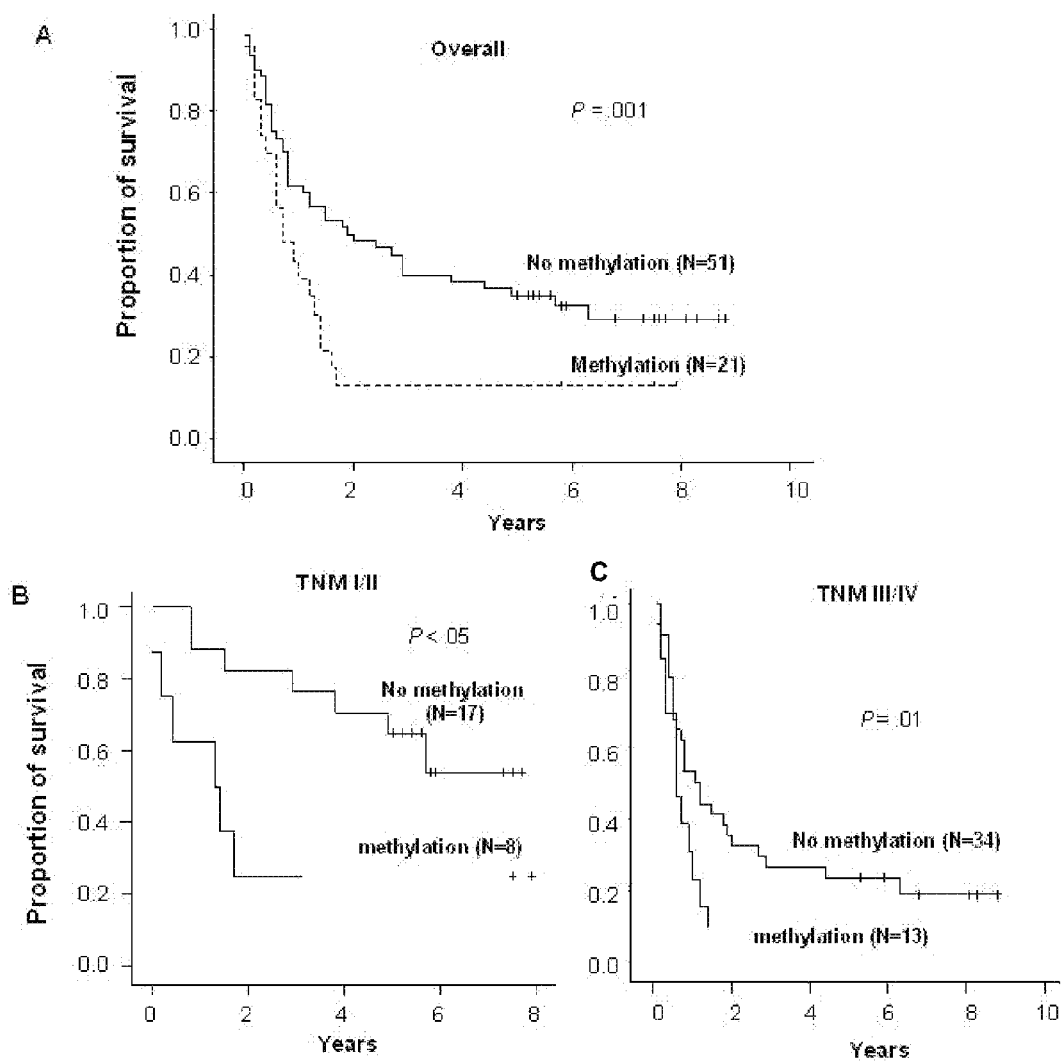
FIGS. 11A, B and C show Kaplan-Meier analysis of GC patient survival. Promoter methylation of ADAMTS9 is associated with poor survival of gastric cancer patients.

As shown in the Kaplan-Meier survival curves, gastric cancer patients with ADAMTS9 methylation had significantly shorter survival than those without ADAMTS9 methylation (P=0.001, log-rank test; FIG. 11). The difference in survival remained significant even if patients were further stratified by tumor TNM staging. The overall survival of patients with ADAMTS9 methylation was significantly shorter than that of other gastric cancer patients in all stages, respectively (FIG. 11).

Expression or methylation of the ADAMTS9 gene is useful as a marker for the diagnosis and prognosis of gastric cancer. Furthermore, methods for inhibiting the growth of gastric cancer include expressing ADAMTS9 or increasing the expression of ADAMTS9 in a patient with gastric cancer.

All publications, including patents, patent applications, and GenBank Accession Numbers, cited herein are hereby incorporated by reference in their entirety for all purposes.

What is claimed is:

1. A method for assessing risk of cancer-related death among gastric cancer patients, comprising the steps of:
   (a) treating gastric tissue samples taken from the patients with a bisulfite;
   (b) performing a methylation-specific polymerase chain reaction to amplify a genomic sequence comprising SEQ ID NO:1 using an oligonucleotide primer consisting of the nucleotide sequence of SEQ ID NO: 10, 11, 12, 13, 14 or 15, and determining whether in each sample genomic sequence of SEQ ID NO:1 is methylated or unmethylated; and
   (c) assigning a higher risk of cancer-related death to a patient whose sample contains methylated genomic sequence of SEQ ID NO:1 and assigning a lower risk of cancer-related death to another patient whose sample contains unmethylated genomic sequence of SEQ ID NO:1.

2. The method of claim 1, wherein the bisulfite is sodium bisulfite.

3. The method of claim 1, wherein step (b) comprises sequencing of a DNA molecule.

4. The method of claim 3, wherein the methylation-specific polymerase chain reaction in step (b) is followed by DNA sequencing.

5. The method of claim 1, wherein the methylation-specific polymerase chain reaction in step (b) uses a pair of oligonucleotide primers having the nucleotide sequence set forth in SEQ ID NOs:10 and 11.

6. The method of claim 1, wherein the methylation-specific polymerase chain reaction in step (b) uses a pair of oligonucleotide primers having the nucleotide sequence set forth in SEQ ID NOs:12 and 13.

7. The method of claim 1, wherein the methylation-specific polymerase chain reaction in step (b) uses a pair of oligonucleotide primers having the nucleotide sequence set forth in SEQ ID NOs:14 and 15.

* * * * *

SEQUENCE LISTING

```
<160> NUMBER OF SEQ ID NOS: 15

<210> SEQ ID NO 1
<211> LENGTH: 438
<212> TYPE: DNA
<213> ORGANISM: Homo sapiens
<220> FEATURE:
<221> NAME/KEY: promoter
<222> LOCATION: (1)...(438)
<223> OTHER INFORMATION: promoter region of human ADAMTS9 (-400 to +38
      from the transcription start site)

<400> SEQUENCE: 1
gggcatttga gaggctgtgg acccgcggcc ccccgcctc cgcccccca gccccccatt        60 caagaagccg ctcagctatc ccggccagca cagggcgccc ggcgcgcctc ggagcgcaag      120
ttcctcgcct tctcctgccc gctcgctggg cattatgcgg ccaagcagcc gagcccagt       180 cctcctcctc ctcctgctcc tccggctcct cctgcggccc gagcggctca gctctcggca      240
ggcggcggcg ttgctcagcc gagcgcagac gggaccctcg cagcgagacc tcagcgactc      300
ctaaagtcaa aagttggcgg cgggcgccgg gctccgcgcg ctctccacgg ccgctgcctc      360
gcgtcgccgc cgcagccaag gagggcagga gggaggggg tgggggcagc ggagggaggg       420
gtgggaagca ccatgcag                                                    438

<210> SEQ ID NO 2
<211> LENGTH: 5808
<212> TYPE: DNA
<213> ORGANISM: Homo sapiens
<220> FEATURE:
<223> OTHER INFORMATION: human ADAMTS9 protein coding cDNA
<220> FEATURE:
<221> NAME/KEY: CDS
<222> LOCATION: (1)...(5808)
<223> OTHER INFORMATION: human ADAMTS9
```

<400> SEQUENCE: 2

```
atgcagtttg tatcctgggc cacactgcta acgctcctgg tgcgggacct ggccgagatg     60
gggagcccag acgccgcggc ggccgtgcgc aaggacaggc tgcacccgag gcaagtgaaa    120
ttattagaga ccctgagcga atacgaaatc gtgtctccca tccgagtgaa cgctctcgga    180
gaaccctttc ccacgaacgt ccacttcaaa agaacgcgac ggagcattaa ctctgccact    240
gacccctggc ctgccttcgc ctcctcctct tcctcctcta cctcctccca ggcgcattac    300
cgcctctctg ccttcggcca gcagtttcta tttaatctca ccgccaatgc cggatttatc    360
gctccactgt tcactgtcac cctcctcggg acgcccgggg tgaatcagac caagttttat    420
tccgaagagg aagcggaact caagcactgt ttctacaaag gctatgtcaa taccaactcc    480
gagcacacgg ccgtcatcag cctctgctca ggaatgctgg gcacattccg gtctcatgat    540
ggggattatt ttattgaacc actacagtct atggatgaac aagaagatga gaggaacaa     600
aacaaacccc acatcattta taggcgcagc gccccccaga gagagccctc aacaggaagg    660
catgcatgtg acacctcaga acacaaaaat aggcacagta agacaagaa gaaaaccaga     720
gcaagaaaat ggggagaaag gattaacctg gctggtgacg tagcagcatt aaacagcggc    780
ttagcaacag aggcattttc tgcttatggt aataagacgg acaacacaag agaaaagagg    840
acccacagaa ggacaaaacg tttttttatcc tatccacggt ttgtagaagt cttggtggtg    900
gcagacaaca gaatggtttc ataccatgga gaaaaccttc aacactatat tttaacttta    960
atgtcaattg tagcctctat ctataaagac ccaagtattg aaatttaat taatattgtt   1020
attgtgaact taattgtgat tcataatgaa caggatgggc cttccatatc ttttaatgct   1080
cagacaaacat taaaaaactt tgccagtgg cagcattcga gaacagtcc aggtggaatc    1140
catcatgata ctgctgttct cttaacaaga caggatatct gcagagctca cgacaaatgt   1200
gataccttag gcctggctga actgggaacc atttgtgatc cctatagaag ctgttctatt   1260
agtgaagata gtggattgag tacagctttt acgatcgccc atgagctggg ccatgtgttt   1320
aacatgcctc atgatgacaa caacaaatgt aaagaagaag gagttaagag tccccagcat   1380
gtcatggctc aacactgaa cttctacacc aaccctggat gtggtcaaa gtgtagtcga    1440
aaatatatca ctgagttttt agacactggt tatggcgagt gtttgcttaa cgaacctgaa   1500
tccagaccct accctttgcc tgtccaactg ccaggcatcc tttacaacgt gaataaacaa   1560
tgtgaattga ttttggacc aggttctcag gtgtgcccat atatgatgca gtgcagacgg   1620
ctctggtgca ataacgtcaa tggagtacac aaaggctgcc ggactcagca cacaccctgg   1680
gccgatggga cggagtgcga gcctggaaag cactgcaagt atggattttg tgttcccaaa   1740
gaaatggatg tccccgtgac agatggatcc tggggaagtt ggagtccctt ggaacctgc    1800
tccagaacat gtggagggg catcaaaaca gccattcgag agtgcaacag accagaacca   1860
aaaaatggtg gaaatactg tgtaggacgt agaatgaaat ttaagtcctg caacacggag   1920
ccatgtctca gcagaagcg agacttccga gatgaacagt gtgctcactt tgacgggaag   1980
cattttaaca tcaacggtct gcttcccaat gtgcgctggg tccctaaata cagtggaatt   2040
ctgatgaagg accggtgcaa gttgttctgc agagtggcag ggaacacagc ctactatcag   2100
cttcgagaca gagtgataga tggaactcct tgtggccagg acacaaatga tatctgtgtc   2160
cagggccttt gccggcaagc tggatgcgat catgttttaa actcaaaagc ccggagagat   2220
aaatgtgggg tttgtggtgg cgataattct tcatgcaaaa cagtggcagg aacatttaat   2280
```

```
acagtacatt atggttacaa tactgtggtc cgaattccag ctggtgctac caatattgat    2340
gtgcggcagc acagtttctc agggaaaaca gacgatgaca actacttagc tttatcaagc    2400
agtaaaggtg aattcttgct aaatggaaac tttgttgtca caatggccaa aagggaaatt    2460
cgcattggga atgctgtggt agagtacagt gggtccgaga ctgccgtaga agaattaac     2520
tcaacagatc gcattgagca agaacttttg cttcaggttt tgtcggtggg aaagttgtac    2580
aaccccgatg tacgctattc tttcaatatt ccaattgaag ataaacctca gcagttttac    2640
tggaacagtc atgggccatg gcaagcatgc agtaaaccct gccaagggga acggaaacga    2700
aaacttgttt gcaccaggga atctgatcag cttactgttt ctgatcaaag atgcgatcgg    2760
ctgccccagc ctggacacat tactgaaccc tgtggtacag actgtgacct gaggtggcat    2820
gttgccagca ggagtgaatg tagtgccag tgtggcttgg gttaccgcac attggacatc     2880
tactgtgcca aatatagcag gctggatggg aagactgaga aggttgatga tggtttttgc    2940
agcagccatc ccaaaccaag caaccgtgaa aaatgctcag gggaatgtaa cacgggtggc    3000
tggcgctatt ctgcctggac tgaatgttca aaaagctgtg acggtgggac ccagaggaga    3060
agggctattt tgtcaatac ccgaaatgat gtactggatg acagcaaatg cacacatcaa      3120
gagaaagtta ccattcagag gtgcagtgag ttcccttgtc cacagtggaa atctggagac    3180
tggtcagagt gcttggtcac ctgtggaaaa gggcataagc accgccaggt ctggtgtcag    3240
tttggtgaag atcgattaaa tgatagaatg tgtgaccctg agaccaagcc aacatctatg    3300
cagacttgtc agcagccgga atgtgcatcc tggcaggcgg gtccctgggg acagtgcagt    3360
gtcacttgtg gacagggata ccagctaaga gcagtgaaat gcatcattgg gacttatatg    3420
tcagtggtag atgacaatga ctgtaatgca gcaactagac caactgatac ccaggactgt    3480
gaattaccat catgtcatcc tcccccagct gccccgaaaa cgaggagaag cacatacagt    3540
gcaccaagaa cccagtggcg atttgggtct tggaccccat gctcagccac ttgtgggaaa    3600
ggtacccgga tgagatacgt cagctgccga gatgagaatg gctctgtggc tgacgagagt    3660
gcctgtgcta ccctgcctag accagtggca aaggaagaat gttctgtgac accctgtggg    3720
caatggaagg ccttggactg gagctcttgc tctgtgacct gtgggcaagg tagggcaacc    3780
cggcaagtga tgtgtgtcaa ctacagtgac cacgtgatcg atcggagtga gtgtgaccag    3840
gattatatcc cagaaactga ccaggactgt tccatgtcac catgccctca aggaccccca    3900
gacagtggct tagctcagca ccccttccaa aatgaggact atcgtccccg gagcgccagc    3960
cccagccgca cccatgtgct cggtggaaac cagtggagaa ctggcccctg ggagcatgt     4020
tccagtacct gtgctggcgg atcccagcgg cgtgttgttg tatgtcagga tgaaaatgga    4080
tacaccgcaa acgactgtgt ggagagaata aaacctgatg agcaaagagc ctgtgaatcc    4140
ggcccttgtc ctcagtgggc ttatggcaac tggggagagt gcactaagct gtgtggtgga    4200
ggcataagaa caagactggt ggtctgtcag cggtccaacg tgaacggtt tccagatttg    4260
agctgtgaaa ttcttgataa acctcccgat cgtgagcagt gtaacacaca tgcttgtcca    4320
cacgacgctg catggagtac tggcccttgg agctcgtgtt ctgtctcttg tggtcgaggg    4380
cataaacaac gaaatgttta ctgcatggca aagatggaa gccatttaga aagtgattac     4440
tgtaagcacc tggctaagcc acatgggcac agaaagtgcc gaggaggaag atgccccaaa    4500
tggaaagctg cgcgcttgga gtcagtgctct gtgtcctgtg gccgaggcgt acagcagagg   4560
catgtgggct gtcagatcgg aacacacaaa atagccagag agaccgagtg caacccatac    4620
accagaccgg agtcggaacg cgactgccaa ggcccacggt gtccctcta cacttggagg      4680
```

-continued

```
gcagaggaat ggcaagaatg caccaagacc tgcggcgaag gctccaggta ccgcaaggtg    4740
gtgtgtgtgg atgacaacaa aaacgaggtg catgggcac gctgtgacgt gagcaagcgg    4800
ccggtggacc gtgaaagctg tagtttgcaa ccctgcgagt atgtctggat cacaggagaa    4860
tggtcagagt gctcagtgac ctgtggaaaa ggctacaaac aaaggcttgt ctcgtgcagc    4920
gagatttaca ccgggaagga gaattatgaa tacagctacc aaaccaccat caactgccca    4980
ggcacgcagc cccccagtgt tcaccctgt tacctgaggg actgccctgt ctcggccacc    5040
tggagagttg gcaactgggg gagctgctca gtgtcttgtg gtgttggagt gatgcagaga    5100
tctgtgcaat gtttaaccaa tgaggaccaa cccagccact tatgccacac tgatctgaag    5160
ccagaagaac gaaaaacctg ccgtaatgtc tataactgtg agttacccca gaattgcaag    5220
gaggtaaaaa gacttaaagg tgccagtgaa atggtgaat atttcctgat gattagagga    5280
aagcttctga agatattctg tgcggggatg cactctgacc accccaaaga gtacgtgaca    5340
ctggtgcatg gagactctga gaatttctcc gaggtttatg gcacaggtt acacaaccca    5400 acagaatgtc cctataacgg gagccggcgc gatgactgcc aatgtcggaa ggattacacg    5460
gccgctgggt tttccagttt tcagaaaatc agaatagacc tgaccagcat gcagataatc    5520
accactgact tacagtttgc aaggacaagc gaaggacatc ccgtcccttt tgccacagcc    5580
ggggattgct acagcgctgc caagtgccca caggtcgtt ttagcatcaa cctttatgga    5640
accggcttgt ctttaactga atctgccaga tggatatcac aagggaatta tgctgtctct    5700
gacatcaaga gtcgccgga tggtacccga gtcgtaggga atgcggtgg ttactgtgga    5760 aaatgcactc catcctctgg tactggcctg gaggtgcgag ttttatag              5808
```

```
<210> SEQ ID NO 3
<211> LENGTH: 7335
<212> TYPE: DNA
<213> ORGANISM: Homo sapiens
<220> FEATURE:
<223> OTHER INFORMATION: ADAM metallopeptidase with thrombospondin type
      1 motif, 9 (ADAMTS9, ADAM-TS9, ADAMTS-9, ADAM-TS 9), disintegrin
      and metalloproteinase (reprolysin type) with thrombospondin motifs
      9 preproprotein cDNA
<220> FEATURE:
<221> NAME/KEY: CDS
<222> LOCATION: (33)...(5840)
<223> OTHER INFORMATION: human ADAMTS9 preproprotein
<220> FEATURE:
<221> NAME/KEY: sig_peptide
<222> LOCATION: (33)...(86)
<223> OTHER INFORMATION: signal peptide
<220> FEATURE:
<221> NAME/KEY: misc_feature
<222> LOCATION: (87)...(5837)
<223> OTHER INFORMATION: proprotein
<220> FEATURE:
<221> NAME/KEY: mat_peptide
<222> LOCATION: (894)...(5837)
<223> OTHER INFORMATION: mature peptide

<400> SEQUENCE: 3
```

```
tgggggcagc ggagggaggg gtgggaagca ccatgcagtt tgtatcctgg gccacactgc      60
taacgctcct ggtgcgggac ctggccgaga tggggagccc agacgccgcg gcggccgtgc     120
gcaaggacag gctgcacccg aggcaagtga aattattaga ccctgagc gaatacgaaa       180 tcgtgtctcc catccgagtg aacgctctcg gagaacccct tcccacgaac gtccacttca     240
aaagaacgcg acgagcatt aactctgcca ctgaccctg gctgccttc gcctcctcct       300 cttcctcctc tacctcctcc caggcgcatt accgcctctc tgccttcggc cagcagtttc     360
```

```
tatttaatct caccgccaat gccggattta tcgctccact gttcactgtc accctcctcg    420
ggacgcccgg ggtgaatcag accaagtttt attccgaaga ggaagcggaa ctcaagcact    480
gtttctacaa aggctatgtc aataccaact ccgagcacac ggccgtcatc agcctctgct    540
caggaatgct gggcacattc cggtctcatg atggggatta ttttattgaa ccactacagt    600
ctatggatga acaagaagat gaagaggaac aaaacaaacc ccacatcatt tataggcgca    660
gcgccccccca gagagagccc tcaacaggaa ggcatgcatg tgacacctca gaacacaaaa   720
ataggcacag taaagacaag aagaaaacca gagcaagaaa atggggagaa aggattaacc    780
tggctggtga cgtagcagca ttaaacagcg gcttagcaac agaggcattt tctgcttatg    840
gtaataagac ggacaacaca agagaaaaga ggacccacag aaggacaaaa cgttttttat    900
cctatccacg gtttgtagaa gtcttggtgg tggcagacaa cagaatggtt tcataccatg    960
gagaaaacct tcaacactat atttttaactt taatgtcaat tgtagcctct atctataaag   1020
acccaagtat tggaaattta attaatattg ttattgtgaa cttaattgtg attcataatg    1080
aacaggatgg gccttccata tcttttaatg ctcagacaac attaaaaaac ttttgccagt    1140
ggcagcattc gaagaacagt ccaggtggaa tccatcatga tactgctgtt ctcttaacaa    1200
gacaggatat ctgcagagct cacgacaaat gtgatacctt aggcctggct gaactgggaa    1260
ccatttgtga tccctataga agctgttcta ttagtgaaga tagtgattg agtacagctt     1320
ttacgatcgc ccatgagctg ggccatgtgt ttaacatgcc tcatgatgac aacaacaaat    1380
gtaaagaaga aggagttaag agtccccagc atgtcatggc tccaacactg aacttctaca    1440
ccaaccccctg gatgtggtca aagtgtagtc gaaaatatat cactgagttt ttagacactg   1500
gttatgcgca gtgtttgctt aacgaacctg aatccagacc ctacccttg cctgtccaac     1560
tgccaggcat cctttacaac gtgaataaac aatgtgaatt gattttttgga ccaggttctc   1620
aggtgtgccc atatatgatg cagtgcagac ggctctggtg caataacgtc aatggagtac    1680
acaaaggctg ccggactcag cacacaccct gggccgatgg gacggagtgc gagcctggaa    1740
agcactgcaa gtatgggattt tgtgttccca aagaaatgga tgtccccgtg acagatggat    1800
cctggggaag ttggagtccc tttggaacct gctccagaac atgtgagggg gcatcaaaa    1860
cagccattcg agagtgcaac agaccagaac caaaaaatgg tggaaaatac tgtgtaggac    1920
gtagaatgaa atttaagtcc tgcaacacgg agccatgtct caagcagaag cgagacttcc    1980
gagatgaaca gtgtgctcac tttgacggga agcattttaa catcaacggt ctgcttccca    2040
atgtgcgctg ggtccctaaa tacagtgaaa ttctgatgaa ggaccggtgc aagttgttct    2100
gcagagtggc agggaacaca gcctactatc agcttcgaga cagagtgata gatggaactc    2160
cttgtggcca ggacacaaat gatatctgtg tccaggccct tgccggcaa gctggatgcg     2220
atcatgtttt aaactcaaaa gcccggagag ataaatgtgg ggtttgtggt ggcgataatt    2280
cttcatgcaa aacagtggca ggaacattta atacagtaca ttatggttac aatactgtgg    2340
tccgaattcc agctggtgct accaatattg atgtgcggca gcacagtttc tcagggaaa    2400
cagacgatga caactactta gctttatcaa gcagtaaagg tgaattcttg ctaaatggaa    2460
actttgttgt cacaatggcc aaaagggaaa ttcgcattgg gaatgctgtg gtagagtaca    2520
gtgggtccga gactgccgta gaaagaatta actcaacaga tcgcattgag caagaacttt    2580
tgcttcaggt tttgtcggtg ggaaagttgt acaaccccga tgtacgctat tctttcaata    2640
ttccaattga agataaacct cagcagtttt actggaacag tcatgggcca tggcaagcat    2700
```

```
gcagtaaacc ctgccaaggg gaacggaaac gaaaacttgt ttgcaccagg gaatctgatc   2760
agcttactgt ttctgatcaa agatgcgatc ggctgcccca gcctggacac attactgaac   2820
cctgtggtac agactgtgac ctgaggtggc atgttgccag caggagtgaa tgtagtgccc   2880
agtgtggctt gggttaccgc acattggaca tctactgtgc caaatatagc aggctggatg   2940
ggaagactga gaaggttgat gatggttttt gcagcagcca tcccaaacca agcaaccgtg   3000
aaaaatgctc aggggaatgt aacacggggtg gctggcgcta ttctgcctgg actgaatgtt   3060
caaaaagctg tgacggtggg acccagagga gaagggctat ttgtgtcaat acccgaaatg   3120
atgtactgga tgacagcaaa tgcacacatc aagagaaagt taccattcag aggtgcagtg   3180
agttcccttg tccacagtgg aaatctggag actggtcaga gtgcttggtc acctgtggaa   3240
aagggcataa gcaccgccag gtctggtgtc agtttggtga agatcgatta atgatagaa    3300 tgtgtgaccc tgagaccaag ccaacatcta tgcagacttg tcagcagccg gaatgtgcat   3360
cctggcaggc gggtccctgg ggacagtgca gtgtcacttg tggacaggga taccagctaa   3420
gagcagtgaa atgcatcatt gggacttata tgtcagtggt agatgacaat gactgtaatg   3480
cagcaactag accaactgat acccaggact gtgaattacc atcatgtcat cctcccccag   3540
ctgccccgga aacgaggaga agcacataca gtgcaccaag aacccagtgg cgatttgggt   3600
cttggacccc atgctcagcc acttgtggga aaggtacccg gatgagatac gtcagctgcc   3660
gagatgagaa tggctctgtg gctgacgaga gtgcctgtgc taccctgcct agaccagtgg   3720
caaaggaaga atgttctgtg acaccctgtg ggcaatggaa ggccttggac tggagctctt   3780
gctctgtgac ctgtgggcaa ggtagggcaa cccggcaagt gatgtgtgtc aactacagtg   3840
accacgtgat cgatcggagt gagtgtgacc aggattatat cccagaaact gaccaggact   3900
gttccatgtc accatgccct caaaggaccc cagacagtgg cttagctcag cacccccttcc  3960 aaaatgagga ctatcgtccc cggagcgcca gccccagccg cacccatgtg ctcggtggaa   4020
accagtggag aactggcccc tggggagcat gttccagtac ctgtgctggc ggatcccagc   4080
ggcgtgttgt tgtatgtcag gatgaaaatg gatacaccgc aaacgactgt gtggagagaa   4140 taaaaacctga tgagcaaaga gcctgtgaat ccggcccttg tcctcagtgg gcttatggca   4200
actggggaga gtgcactaag ctgtgtggtg gaggcataag aacaagactg gtggtctgtc   4260
agcggtccaa cggtgaacgg tttccagatt tgagctgtga aattcttgat aaacctcccg   4320
atcgtgagca gtgtaacaca catgcttgtc cacacgacgc tgcatggagt actggcccctt  4380 ggagctcgtg ttctgtctct tgtggtcgag gcataaaca acgaaatgtt tactgcatgg    4440
caaaagatgg aagccatttta gaaagtgatt actgtaagca cctggctaag ccacatgggc  4500
acagaaagtg ccgaggagga agatgcccca atggaaagc tggcgcttgg agtcagtgct    4560
ctgtgtcctg tggccgaggc gtacagcaga ggcatgtggg ctgtcagatc ggaacacaca   4620
aaatagccag agagaccgag tgcaacccat acaccagacc ggagtcggaa cgcgactgcc   4680
aaggcccacg gtgtccctc tacacttgga gggcagagga atggcaagaa tgcaccaaga    4740
cctgcggcga aggctccagg taccgcaagg tggtgtgtgt ggatgacaac aaaaacgagg   4800 tgcatgggc acgctgtgac gtgagcaagc ggccggtgga ccgtgaaagc tgtagtttgc    4860
aaccctgcga gtatgtctgg atcacaggag aatggtcaga gtgctcagtg acctgtggaa   4920
aaggctacaa acaaaggctt gtctcgtgca gcgagattta caccgggaag gagaattatg   4980
aatacagcta ccaaaccacc atcaactgcc caggcacgca gccccccagt gttcacccct    5040
gttacctgag ggactgccct gtctcggcca cctggagagt tggcaactgg gggagctgct   5100
```

```
cagtgtcttg tggtgttgga gtgatgcaga gatctgtgca atgtttaacc aatgaggacc    5160
aacccagcca cttatgccac actgatctga agccagaaga acgaaaaacc tgccgtaatg    5220
tctataactg tgagttaccc cagaattgca aggaggtaaa aagacttaaa ggtgccagtg    5280
aagatggtga atatttcctg atgattagag gaaagcttct gaagatattc tgtgcgggga    5340
tgcactctga ccaccccaaa gagtacgtga cactggtgca tggagactct gagaatttct    5400
ccgaggttta tgggcacagg ttacacaacc aacagaatg tccctataac gggagccggc     5460
gcgatgactg ccaatgtcgg aaggattaca cggccgctgg gttttccagt tttcagaaaa    5520
tcagaataga cctgaccagc atgcagataa tcaccactga cttacagttt gcaaggacaa    5580
gcgaaggaca tcccgtccct tttgccacag ccggggattg ctacagcgct gccaagtgcc    5640
cacagggtcg ttttagcatc aacctttatg aaccggctt gtctttaact gaatctgcca     5700
gatggatatc acaagggaat tatgctgtct ctgacatcaa gaagtcgccg gatggtaccc    5760
gagtcgtagg gaaatgcggt ggttactgtg gaaaatgcac tccatcctct ggtactggcc    5820
tggaggtgcg agttttatag ctaaggtgct ttgaagagga agccattatg gatggatgaa    5880
ggatagtaat gcaataccte caccttaatt tgggtgcatg tgtatgtgtg tgtgtgtttg    5940
tgtgtgactt gtatgcttgt gtgtgtaaat gtgtgtacat atacatatat acatatctac    6000
acatacatat atacacatat atgtgtgtat gtagatatgt agactatcct aatgatgtaa    6060
agtttaatat ttatgtttga aattatttat tgtgatgtaa tatttttgta cgtaaaatga    6120
ttctattatg actgcctttg catgtagtaa tatgacaaag tgatccttca ttatcacggt    6180
acactattgt ttacttttca tctgtaaatg ttttattgtt actttttaa aatgaatttt      6240 tttaaaacaa tctagccatc atcaaggtgc tataagagtt gtataaaaga tatttttggc    6300
atttctaggc aagtatcagc caataagtat gttagtgata tcacagattg taccaactat    6360
taactatgtt aaataagtat tcagtttcat gtgatctctg ggaaaaaaat atgctgcctt    6420
ggtgctaata ttgtatgtat ttaaatgatc atccgactca gaaatataaa cacttttaat    6480
gaaagggagg aacggaagga caatttccag tgcacagaat cacttggatg aaataagacc    6540
agctctttac ccttattttt ggatatgcct tttttggaag agacttagac tttatcctta    6600
ttgttgttag tgttgttaat attcgttgct tcagcccacg gtgccttggt ctctccacaa    6660
tcaaatggag gatcccccaa gcagcttcat tacagagtga tattgggaaa gtgagatcct    6720
ctcaccattt tgccaagata ctctaaaatg acatccaagt ttaccagtag aaagacacag    6780
gatgcacaga atgggcatga ccttcagctc acgagcacac ctggagaaat tcagaaccag    6840
gttctgaatc atcacgattg cctttttgcat gaaaacatcg gctggtgatg tgacttctct    6900
tcaggccatg agcctaacac cctgccggtt ttcatgcccg ctgcagtaat ggacgtttgt    6960
gtgaagaaat gaactgtgga gtacaaaatg ctttgagtct ttccgattgc tcattaattc    7020
acttttttgt tacttctttc caaaatggaa gtgctgaagc catggtcttt ctgcccctcc    7080
aagctgatga agggaagcct ttgccaatgg cccatggaag acacttggtt tgagaaaccc    7140
tgcccacttc caaagaccaa agagattagg aaaagcctgg cagtattctc caactccaaa    7200
caagctctag agtgctccag gaaaagttat attcagtata tgaataagtg ttattctcca    7260
ttattaatgt gttctgaaaa tatattatga ataaatacat caccacaccc aaaaaaaaaa    7320
aaaaaaaaaa aaaaa                                                     7335

<210> SEQ ID NO 4
```

```
<211> LENGTH: 144
<212> TYPE: DNA
<213> ORGANISM: Homo sapiens
<220> FEATURE:
<223> OTHER INFORMATION: partial coding sequence used to detect human
      ADAMTS9 mRNA

<400> SEQUENCE: 4
caataccaac tccgagcaca cggccgtcat cagcctctgc tcaggaatgc tgggcacatt     60
ccggtctcat gatggggatt attttattga accactacag tctatggatg aacaagaaga    120
tgaagaggaa caaaacaaac ccca                                           144

<210> SEQ ID NO 5
<211> LENGTH: 1935
<212> TYPE: PRT
<213> ORGANISM: Homo sapiens
<220> FEATURE:
<223> OTHER INFORMATION: ADAM metallopeptidase with thrombospondin type
      1 motif, 9 (ADAMTS9, ADAM-TS9, ADAMTS-9, ADAM-TS 9),
      disintegrin and metalloproteinase (reprolysin
      type) with thrombospondin motifs 9 preproprotein
<220> FEATURE:
<221> NAME/KEY: SIGNAL
<222> LOCATION: (1)...(18)
<223> OTHER INFORMATION: signal peptide
<220> FEATURE:
<221> NAME/KEY: PROPEP
<222> LOCATION: (19)...(1935)
<223> OTHER INFORMATION: proprotein
<220> FEATURE:
<221> NAME/KEY: PEPTIDE
<222> LOCATION: (288)...(1935)
<223> OTHER INFORMATION: mature peptide

<400> SEQUENCE: 5

Met Gln Phe Val Ser Trp Ala Thr Leu Leu Thr Leu Leu Val Arg Asp
 1               5                  10                  15

Leu Ala Glu Met Gly Ser Pro Asp Ala Ala Ala Val Arg Lys Asp
             20                  25                  30

Arg Leu His Pro Arg Gln Val Lys Leu Leu Glu Thr Leu Ser Glu Tyr
         35                  40                  45

Glu Ile Val Ser Pro Ile Arg Val Asn Ala Leu Gly Glu Pro Phe Pro
     50                  55                  60

Thr Asn Val His Phe Lys Arg Thr Arg Arg Ser Ile Asn Ser Ala Thr
 65                  70                  75                  80

Asp Pro Trp Pro Ala Phe Ala Ser Ser Ser Ser Ser Thr Ser Ser
                 85                  90                  95

Gln Ala His Tyr Arg Leu Ser Ala Phe Gly Gln Gln Phe Leu Phe Asn
            100                 105                 110

Leu Thr Ala Asn Ala Gly Phe Ile Ala Pro Leu Phe Thr Val Thr Leu
        115                 120                 125

Leu Gly Thr Pro Gly Val Asn Gln Thr Lys Phe Tyr Ser Glu Glu Glu
    130                 135                 140

Ala Glu Leu Lys His Cys Phe Tyr Lys Gly Tyr Val Asn Thr Asn Ser
145                 150                 155                 160

Glu His Thr Ala Val Ile Ser Leu Cys Ser Gly Met Leu Gly Thr Phe
                165                 170                 175

Arg Ser His Asp Gly Asp Tyr Phe Ile Glu Pro Leu Gln Ser Met Asp
            180                 185                 190

Glu Gln Glu Asp Glu Glu Glu Gln Asn Lys Pro His Ile Ile Tyr Arg
        195                 200                 205
```

```
Arg Ser Ala Pro Gln Arg Glu Pro Ser Thr Gly Arg His Ala Cys Asp
    210             215                 220

Thr Ser Glu His Lys Asn Arg His Ser Lys Asp Lys Lys Lys Thr Arg
225             230                 235                 240

Ala Arg Lys Trp Gly Glu Arg Ile Asn Leu Ala Gly Asp Val Ala Ala
                245                 250                 255

Leu Asn Ser Gly Leu Ala Thr Glu Ala Phe Ser Ala Tyr Gly Asn Lys
            260                 265                 270

Thr Asp Asn Thr Arg Glu Lys Arg Thr His Arg Arg Thr Lys Arg Phe
        275                 280                 285

Leu Ser Tyr Pro Arg Phe Val Glu Val Leu Val Val Ala Asp Asn Arg
    290                 295                 300

Met Val Ser Tyr His Gly Glu Asn Leu Gln His Tyr Ile Leu Thr Leu
305             310                 315                 320

Met Ser Ile Val Ala Ser Ile Tyr Lys Asp Pro Ser Ile Gly Asn Leu
                325                 330                 335

Ile Asn Ile Val Ile Val Asn Leu Ile Val Ile His Asn Glu Gln Asp
            340                 345                 350

Gly Pro Ser Ile Ser Phe Asn Ala Gln Thr Thr Leu Lys Asn Phe Cys
        355                 360                 365

Gln Trp Gln His Ser Lys Asn Ser Pro Gly Gly Ile His His Asp Thr
    370                 375                 380

Ala Val Leu Leu Thr Arg Gln Asp Ile Cys Arg Ala His Asp Lys Cys
385             390                 395                 400

Asp Thr Leu Gly Leu Ala Glu Leu Gly Thr Ile Cys Asp Pro Tyr Arg
                405                 410                 415

Ser Cys Ser Ile Ser Glu Asp Ser Gly Leu Ser Thr Ala Phe Thr Ile
            420                 425                 430

Ala His Glu Leu Gly His Val Phe Asn Met Pro His Asp Asp Asn Asn
        435                 440                 445

Lys Cys Lys Glu Glu Gly Val Lys Ser Pro Gln His Val Met Ala Pro
    450                 455                 460

Thr Leu Asn Phe Tyr Thr Asn Pro Trp Met Trp Ser Lys Cys Ser Arg
465             470                 475                 480

Lys Tyr Ile Thr Glu Phe Leu Asp Thr Gly Tyr Gly Glu Cys Leu Leu
                485                 490                 495

Asn Glu Pro Glu Ser Arg Pro Tyr Pro Leu Pro Val Gln Leu Pro Gly
            500                 505                 510

Ile Leu Tyr Asn Val Asn Lys Gln Cys Glu Leu Ile Phe Gly Pro Gly
        515                 520                 525

Ser Gln Val Cys Pro Tyr Met Met Gln Cys Arg Arg Leu Trp Cys Asn
    530                 535                 540

Asn Val Asn Gly Val His Lys Gly Cys Arg Thr Gln His Thr Pro Trp
545             550                 555                 560

Ala Asp Gly Thr Glu Cys Glu Pro Gly Lys His Cys Lys Tyr Gly Phe
                565                 570                 575

Cys Val Pro Lys Glu Met Asp Val Pro Val Thr Asp Gly Ser Trp Gly
            580                 585                 590

Ser Trp Ser Pro Phe Gly Thr Cys Ser Arg Thr Cys Gly Gly Gly Ile
        595                 600                 605

Lys Thr Ala Ile Arg Glu Cys Asn Arg Pro Glu Pro Lys Asn Gly Gly
    610                 615                 620

Lys Tyr Cys Val Gly Arg Arg Met Lys Phe Lys Ser Cys Asn Thr Glu
```

-continued

```
            625                 630                 635                 640
        Pro Cys Leu Lys Gln Lys Arg Asp Phe Arg Asp Glu Gln Cys Ala His
                            645                 650                 655
        Phe Asp Gly Lys His Phe Asn Ile Asn Gly Leu Leu Pro Asn Val Arg
                            660                 665                 670
        Trp Val Pro Lys Tyr Ser Gly Ile Leu Met Lys Asp Arg Cys Lys Leu
                            675                 680                 685
        Phe Cys Arg Val Ala Gly Asn Thr Ala Tyr Tyr Gln Leu Arg Asp Arg
                            690                 695                 700
        Val Ile Asp Gly Thr Pro Cys Gly Gln Asp Thr Asn Asp Ile Cys Val
        705                 710                 715                 720
        Gln Gly Leu Cys Arg Gln Ala Gly Cys Asp His Val Leu Asn Ser Lys
                            725                 730                 735
        Ala Arg Arg Asp Lys Cys Gly Val Cys Gly Gly Asp Asn Ser Ser Cys
                            740                 745                 750
        Lys Thr Val Ala Gly Thr Phe Asn Thr Val His Tyr Gly Tyr Asn Thr
                            755                 760                 765
        Val Val Arg Ile Pro Ala Gly Ala Thr Asn Ile Asp Val Arg Gln His
                            770                 775                 780
        Ser Phe Ser Gly Glu Thr Asp Asp Asn Tyr Leu Ala Leu Ser Ser
        785                 790                 795                 800
        Ser Lys Gly Glu Phe Leu Leu Asn Gly Asn Phe Val Val Thr Met Ala
                            805                 810                 815
        Lys Arg Glu Ile Arg Ile Gly Asn Ala Val Val Glu Tyr Ser Gly Ser
                            820                 825                 830
        Glu Thr Ala Val Glu Arg Ile Asn Ser Thr Asp Arg Ile Glu Gln Glu
                            835                 840                 845
        Leu Leu Leu Gln Val Leu Ser Val Gly Lys Leu Tyr Asn Pro Asp Val
                            850                 855                 860
        Arg Tyr Ser Phe Asn Ile Pro Ile Glu Asp Lys Pro Gln Gln Phe Tyr
        865                 870                 875                 880
        Trp Asn Ser His Gly Pro Trp Gln Ala Cys Ser Lys Pro Cys Gln Gly
                            885                 890                 895
        Glu Arg Lys Arg Lys Leu Val Cys Thr Arg Glu Ser Asp Gln Leu Thr
                            900                 905                 910
        Val Ser Asp Gln Arg Cys Asp Arg Leu Pro Gln Pro Gly His Ile Thr
                            915                 920                 925
        Glu Pro Cys Gly Thr Asp Cys Asp Leu Arg Trp His Val Ala Ser Arg
                            930                 935                 940
        Ser Glu Cys Ser Ala Gln Cys Gly Leu Gly Tyr Arg Thr Leu Asp Ile
        945                 950                 955                 960
        Tyr Cys Ala Lys Tyr Ser Arg Leu Asp Gly Lys Thr Glu Lys Val Asp
                            965                 970                 975
        Asp Gly Phe Cys Ser Ser His Pro Lys Pro Ser Asn Arg Glu Lys Cys
                            980                 985                 990
        Ser Gly Glu Cys Asn Thr Gly Gly Trp Arg Tyr Ser Ala Trp Thr Glu
                            995                 1000                1005
        Cys Ser Lys Ser Cys Asp Gly Gly Thr Gln Arg Arg Ala Ile Cys
                            1010                1015                1020
        Val Asn Thr Arg Asn Asp Val Leu Asp Asp Ser Lys Cys Thr His Gln
        1025                1030                1035                1040
        Glu Lys Val Thr Ile Gln Arg Cys Ser Glu Phe Pro Cys Pro Gln Trp
                            1045                1050                1055
```

```
Lys Ser Gly Asp Trp Ser Glu Cys Leu Val Thr Cys Gly Lys Gly His
            1060                1065                1070

Lys His Arg Gln Val Trp Cys Gln Phe Gly Glu Asp Arg Leu Asn Asp
        1075                1080                1085

Arg Met Cys Asp Pro Glu Thr Lys Pro Thr Ser Met Gln Thr Cys Gln
        1090                1095                1100

Gln Pro Glu Cys Ala Ser Trp Gln Ala Gly Pro Trp Gly Gln Cys Ser
1105                1110                1115                1120

Val Thr Cys Gly Gln Gly Tyr Gln Leu Arg Ala Val Lys Cys Ile Ile
            1125                1130                1135

Gly Thr Tyr Met Ser Val Val Asp Asp Asn Asp Cys Asn Ala Ala Thr
            1140                1145                1150

Arg Pro Thr Asp Thr Gln Asp Cys Glu Leu Pro Ser Cys His Pro Pro
        1155                1160                1165

Pro Ala Ala Pro Glu Thr Arg Arg Ser Thr Tyr Ser Ala Pro Arg Thr
        1170                1175                1180

Gln Trp Arg Phe Gly Ser Trp Thr Pro Cys Ser Ala Thr Cys Gly Lys
1185                1190                1195                1200

Gly Thr Arg Met Arg Tyr Val Ser Cys Arg Asp Glu Asn Gly Ser Val
            1205                1210                1215

Ala Asp Glu Ser Ala Cys Ala Thr Leu Pro Arg Pro Val Ala Lys Glu
            1220                1225                1230

Glu Cys Ser Val Thr Pro Cys Gly Gln Trp Lys Ala Leu Asp Trp Ser
        1235                1240                1245

Ser Cys Ser Val Thr Cys Gly Gln Gly Arg Ala Thr Arg Gln Val Met
        1250                1255                1260

Cys Val Asn Tyr Ser Asp His Val Ile Asp Arg Ser Glu Cys Asp Gln
1265                1270                1275                1280

Asp Tyr Ile Pro Glu Thr Asp Gln Asp Cys Ser Met Ser Pro Cys Pro
        1285                1290                1295

Gln Arg Thr Pro Asp Ser Gly Leu Ala Gln His Pro Phe Gln Asn Glu
        1300                1305                1310

Asp Tyr Arg Pro Arg Ser Ala Ser Pro Ser Arg Thr His Val Leu Gly
        1315                1320                1325

Gly Asn Gln Trp Arg Thr Gly Pro Trp Gly Ala Cys Ser Ser Thr Cys
        1330                1335                1340

Ala Gly Gly Ser Gln Arg Arg Val Val Val Cys Gln Asp Glu Asn Gly
1345                1350                1355                1360

Tyr Thr Ala Asn Asp Cys Val Glu Arg Ile Lys Pro Asp Glu Gln Arg
            1365                1370                1375

Ala Cys Glu Ser Gly Pro Cys Pro Gln Trp Ala Tyr Gly Asn Trp Gly
            1380                1385                1390

Glu Cys Thr Lys Leu Cys Gly Gly Gly Ile Arg Thr Arg Leu Val Val
        1395                1400                1405

Cys Gln Arg Ser Asn Gly Glu Arg Phe Pro Asp Leu Ser Cys Glu Ile
        1410                1415                1420

Leu Asp Lys Pro Pro Asp Arg Glu Gln Cys Asn Thr His Ala Cys Pro
1425                1430                1435                1440

His Asp Ala Ala Trp Ser Thr Gly Pro Trp Ser Ser Cys Ser Val Ser
            1445                1450                1455

Cys Gly Arg Gly His Lys Gln Arg Asn Val Tyr Cys Met Ala Lys Asp
            1460                1465                1470
```

-continued

```
Gly Ser His Leu Glu Ser Asp Tyr Cys Lys His Leu Ala Lys Pro His
            1475                1480                1485
Gly His Arg Lys Cys Arg Gly Arg Cys Pro Lys Trp Lys Ala Gly
1490                1495                1500
Ala Trp Ser Gln Cys Ser Val Ser Cys Gly Arg Gly Val Gln Gln Arg
1505                1510                1515                1520
His Val Gly Cys Gln Ile Gly Thr His Lys Ile Ala Arg Glu Thr Glu
            1525                1530                1535
Cys Asn Pro Tyr Thr Arg Pro Glu Ser Glu Arg Asp Cys Gln Gly Pro
            1540                1545                1550
Arg Cys Pro Leu Tyr Thr Trp Arg Ala Glu Glu Trp Gln Glu Cys Thr
            1555                1560                1565
Lys Thr Cys Gly Glu Gly Ser Arg Tyr Arg Lys Val Val Cys Val Asp
            1570                1575                1580
Asp Asn Lys Asn Glu Val His Gly Ala Arg Cys Asp Val Ser Lys Arg
1585                1590                1595                1600
Pro Val Asp Arg Glu Ser Cys Ser Leu Gln Pro Cys Glu Tyr Val Trp
            1605                1610                1615
Ile Thr Gly Glu Trp Ser Glu Cys Ser Val Thr Cys Gly Lys Gly Tyr
            1620                1625                1630
Lys Gln Arg Leu Val Ser Cys Ser Glu Ile Tyr Thr Gly Lys Glu Asn
            1635                1640                1645
Tyr Glu Tyr Ser Tyr Gln Thr Thr Ile Asn Cys Pro Gly Thr Gln Pro
            1650                1655                1660
Pro Ser Val His Pro Cys Tyr Leu Arg Asp Cys Pro Val Ser Ala Thr
1665                1670                1675                1680
Trp Arg Val Gly Asn Trp Gly Ser Cys Ser Val Ser Cys Gly Val Gly
            1685                1690                1695
Val Met Gln Arg Ser Val Gln Cys Leu Thr Asn Glu Asp Gln Pro Ser
            1700                1705                1710
His Leu Cys His Thr Asp Leu Lys Pro Glu Glu Arg Lys Thr Cys Arg
            1715                1720                1725
Asn Val Tyr Asn Cys Glu Leu Pro Gln Asn Cys Lys Glu Val Lys Arg
            1730                1735                1740
Leu Lys Gly Ala Ser Glu Asp Gly Glu Tyr Phe Leu Met Ile Arg Gly
1745                1750                1755                1760
Lys Leu Leu Lys Ile Phe Cys Ala Gly Met His Ser Asp His Pro Lys
            1765                1770                1775
Glu Tyr Val Thr Leu Val His Gly Asp Ser Glu Asn Phe Ser Glu Val
            1780                1785                1790
Tyr Gly His Arg Leu His Asn Pro Thr Glu Cys Pro Tyr Asn Gly Ser
            1795                1800                1805
Arg Arg Asp Asp Cys Gln Cys Arg Lys Asp Tyr Thr Ala Ala Gly Phe
            1810                1815                1820
Ser Ser Phe Gln Lys Ile Arg Ile Asp Leu Thr Ser Met Gln Ile Ile
1825                1830                1835                1840
Thr Thr Asp Leu Gln Phe Ala Arg Thr Ser Glu Gly His Pro Val Pro
            1845                1850                1855
Phe Ala Thr Ala Gly Asp Cys Tyr Ser Ala Ala Lys Cys Pro Gln Gly
            1860                1865                1870
Arg Phe Ser Ile Asn Leu Tyr Gly Thr Gly Leu Ser Leu Thr Glu Ser
            1875                1880                1885
Ala Arg Trp Ile Ser Gln Gly Asn Tyr Ala Val Ser Asp Ile Lys Lys
```

```
                    1890                1895                1900

Ser Pro Asp Gly Thr Arg Val Val Gly Lys Cys Gly Gly Tyr Cys Gly
1905                1910                1915                1920

Lys Cys Thr Pro Ser Ser Gly Thr Gly Leu Glu Val Arg Val Leu
                    1925                1930                1935
```

<210> SEQ ID NO 6
<211> LENGTH: 114
<212> TYPE: DNA
<213> ORGANISM: Homo sapiens
<220> FEATURE:
<221> NAME/KEY: promoter
<222> LOCATION: (1)...(114)
<223> OTHER INFORMATION: ADAMTS9 promoter region (-280 to -167 from
      transcription start site)

<400> SEQUENCE: 6
ttcctcgcct tctcctgccc gctcgctggg cattatgcgg ccaagcagcc gagccccagt    60
cctcctcctc ctcctgctcc tccggctcct cctgcggccc gagcggctca gctc         114

<210> SEQ ID NO 7
<211> LENGTH: 117
<212> TYPE: DNA
<213> ORGANISM: Homo sapiens
<220> FEATURE:
<221> NAME/KEY: promoter
<222> LOCATION: (1)...(117)
<223> OTHER INFORMATION: ADAMTS9 promoter region (-281 to -165 from
      transcription start site)

<400> SEQUENCE: 7
gttcctcgcc ttctcctgcc cgctcgctgg gcattatgcg gccaagcagc cgagccccag    60
tcctcctcct cctcctgctc ctccggctcc tcctgcggcc cgagcggctc agctctc      117

<210> SEQ ID NO 8
<211> LENGTH: 20
<212> TYPE: DNA
<213> ORGANISM: Artificial Sequence
<220> FEATURE:
<223> OTHER INFORMATION: synthetic RT-PCR forward primer ADAMTS9-F for
      detecting ADAMTS9 mRNA expression

<400> SEQUENCE: 8
caataccaac tccgagcaca                                                20

<210> SEQ ID NO 9
<211> LENGTH: 20
<212> TYPE: DNA
<213> ORGANISM: Artificial Sequence
<220> FEATURE:
<223> OTHER INFORMATION: synthetic RT-PCR reverse primer ADAMTS9-R for
      detecting ADAMTS9 mRNA expression

<400> SEQUENCE: 9
tggggtttgt tttgttcctc                                                20

<210> SEQ ID NO 10
<211> LENGTH: 24
<212> TYPE: DNA
<213> ORGANISM: Artificial Sequence
<220> FEATURE:
<223> OTHER INFORMATION: synthetic bisulfite genomic sequencing (BGS)
      forward primer ADAMTS9-BGS-F

<400> SEQUENCE: 10

```
gggggtatttg agaggttgtg gatt                                           24
```

<210> SEQ ID NO 11
<211> LENGTH: 23
<212> TYPE: DNA
<213> ORGANISM: Artificial Sequence
<220> FEATURE:
<223> OTHER INFORMATION: synthetic bisulfite genomic sequencing (BGS)
      reverse primer ADAMTS9-BGS-R

<400> SEQUENCE: 11

```
ctacataata cttcccaccc ctc                                             23
```

<210> SEQ ID NO 12
<211> LENGTH: 24
<212> TYPE: DNA
<213> ORGANISM: Artificial Sequence
<220> FEATURE:
<223> OTHER INFORMATION: synthetic methylation-specific polymerase chain
      reaction (MSP) methylation specific forward primer
      ADAMTS9-MSP-MF

<400> SEQUENCE: 12

```
tttttcgttt tttttttgttc gttc                                           24
```

<210> SEQ ID NO 13
<211> LENGTH: 20
<212> TYPE: DNA
<213> ORGANISM: Artificial Sequence
<220> FEATURE:
<223> OTHER INFORMATION: synthetic methylation-specific polymerase chain
      reaction (MSP) methylation specific reverse primer
      ADAMTS9-MSP-MR

<400> SEQUENCE: 13

```
aaactaaacc gctcgaaccg                                                 20
```

<210> SEQ ID NO 14
<211> LENGTH: 25
<212> TYPE: DNA
<213> ORGANISM: Artificial Sequence
<220> FEATURE:
<223> OTHER INFORMATION: synthetic methylation-specific polymerase chain
      reaction (MSP) unmethylation specific forward
      primer ADAMTS9-MSP-UF

<400> SEQUENCE: 14

```
gtttttttgtt tttttttgtt tgttt                                          25
```

<210> SEQ ID NO 15
<211> LENGTH: 22
<212> TYPE: DNA
<213> ORGANISM: Artificial Sequence
<220> FEATURE:
<223> OTHER INFORMATION: synthetic methylation-specific polymerase chain
      reaction (MSP) unmethylation specific reverse
      primer ADAMTS9-MSP-UR

<400> SEQUENCE: 15

```
aaaaactaaa ccactcaaac ca                                              22
```